US012691206B2

(12) United States Patent
Wajtryt et al.

(10) Patent No.: US 12,691,206 B2
(45) Date of Patent: Jul. 28, 2026

(54) BREAST PUMP AND METHOD FOR OPERATING SUCH PUMP

(71) Applicant: MEDELA HOLDING AG, Baar (CH)

(72) Inventors: Krzysztof Wajtryt, Baar (CH); Jakub Piotr Pawlowski, Zug (CH); Daria Schelling, Zurich (CH); Beda Weber, Sins (CH); Romana Gander, Thalwil (CH)

(73) Assignee: MEDELA HOLDING AG, Baar (CH)

( * ) Notice: Subject to any disclaimer, the term of this patent is extended or adjusted under 35 U.S.C. 154(b) by 419 days.

(21) Appl. No.: 18/571,537

(22) PCT Filed: Jun. 23, 2022

(86) PCT No.: PCT/EP2022/067266
§ 371 (c)(1),
(2) Date: Dec. 18, 2023

(87) PCT Pub. No.: WO2022/268998
PCT Pub. Date: Dec. 29, 2022

(65) Prior Publication Data
US 2024/0285835 A1    Aug. 29, 2024

(30) Foreign Application Priority Data

Jun. 24, 2021   (EP) ..................................... 21181505

(51) Int. Cl.
*A61M 1/06*      (2006.01)
*A61M 1/00*      (2006.01)

(52) U.S. Cl.
CPC .............. *A61M 1/067* (2021.05); *A61M 1/82* (2021.05)

(58) Field of Classification Search
CPC ........ A61M 1/06; A61M 1/062; A61M 1/064; A61M 1/066; A61M 1/067; A61M 1/068;
(Continued)

(56) References Cited

U.S. PATENT DOCUMENTS 8,702,649 B2   4/2014   Schwartz et al.
10,639,407 B2   5/2020   Weber et al.
(Continued)

FOREIGN PATENT DOCUMENTS

EP      3171906 B1    9/2019
EP      3 373 997 B1    4/2020
(Continued)

OTHER PUBLICATIONS

European Search Report for Application No. 21181505.5, dated Dec. 23, 2021.
(Continued)

*Primary Examiner* — Dung T Ulsh
(74) *Attorney, Agent, or Firm* — MARSHALL, GERSTEIN & BORUN LLP

(57) ABSTRACT

A breast pump shaped at least in part to fit inside a bra and comprising a housing including an aggregate, a breast shield element including a nipple tunnel adapted to receive a nipple, and a milk container adapted to contain a predetermined amount of expressed milk, wherein the breast shield element and the milk container are detachable from the housing. The present invention proposes an aggregate including a piston adapted to reciprocate within the housing, which piston moves the membrane. In the method expressed milk flows from a nipple chamber, which when the breast shield element is laid against a breast is defined in the nipple tunnel between a free end of the nipple tunnel and the breast, through the milk outlet valve into the pumping chamber and from the pumping chamber through the container valve into the milk chamber.

17 Claims, 15 Drawing Sheets

(58) Field of Classification Search
CPC ................ A61M 1/069; A61M 1/0693; A61M
1/06935; A61M 1/0697
See application file for complete search history.

(56) References Cited

U.S. PATENT DOCUMENTS

| | | | |
|---|---|---|---|
| 2010/0262072 A1 | 10/2010 | Attolini et al. | |
| 2021/0121614 A1* | 4/2021 | Schlienger .......... | A61M 1/0697 |

FOREIGN PATENT DOCUMENTS

| | | | |
|---|---|---|---|
| EP | 3 777 911 A1 | 2/2021 |
| WO | WO-2017/139437 A1 | 8/2017 |
| WO | WO-2018/210685 A1 | 11/2018 |
| WO | WO-2018/229504 A1 | 12/2018 |
| WO | WO-2019/080995 A1 | 5/2019 |
| WO | WO-2019/145163 A1 | 8/2019 |

OTHER PUBLICATIONS

International Search Report and Written Opinion for Application
No. PCT/EP2022/067266, dated Oct. 5, 2022.

* cited by examiner

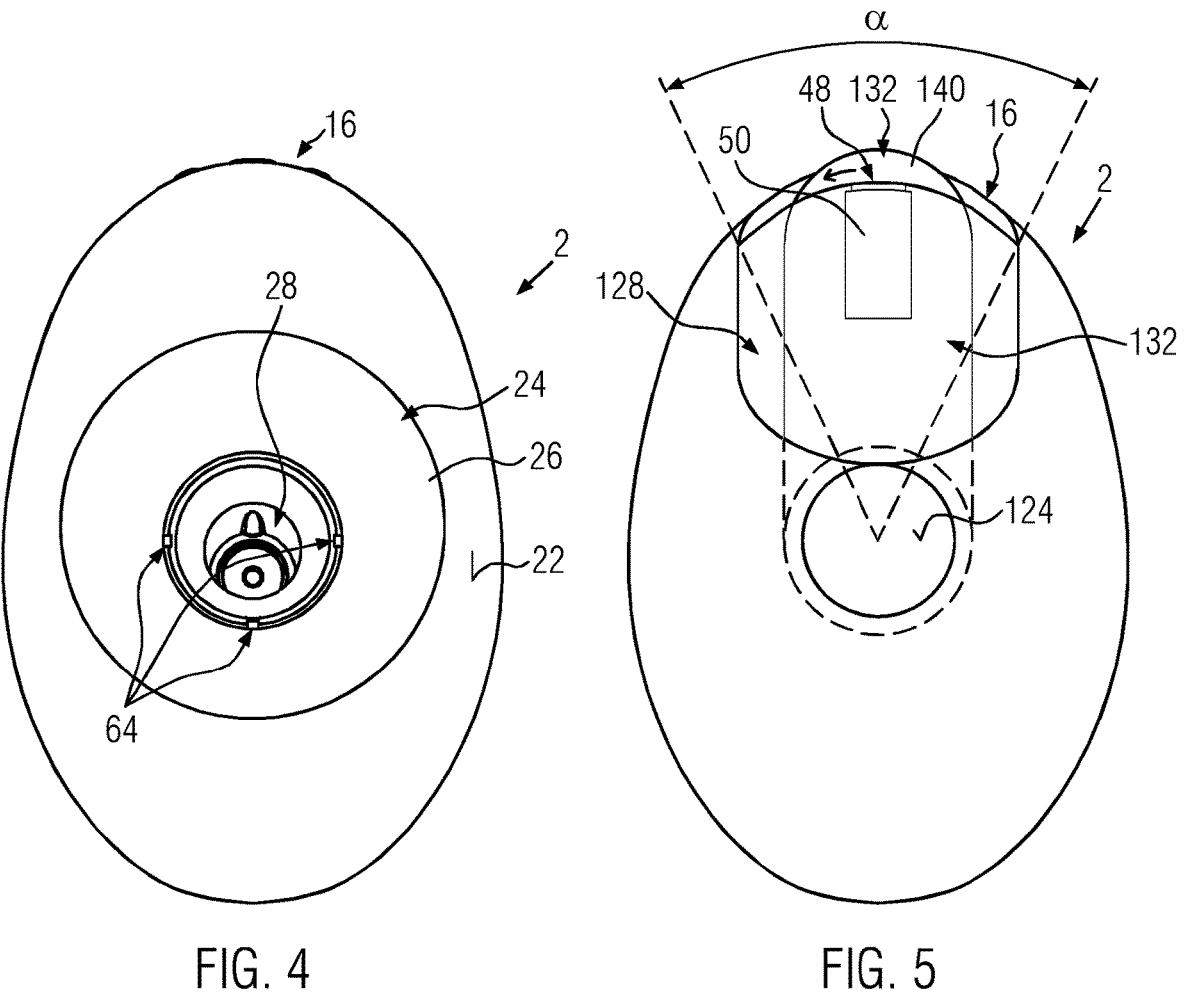
FIG. 4                    FIG. 5

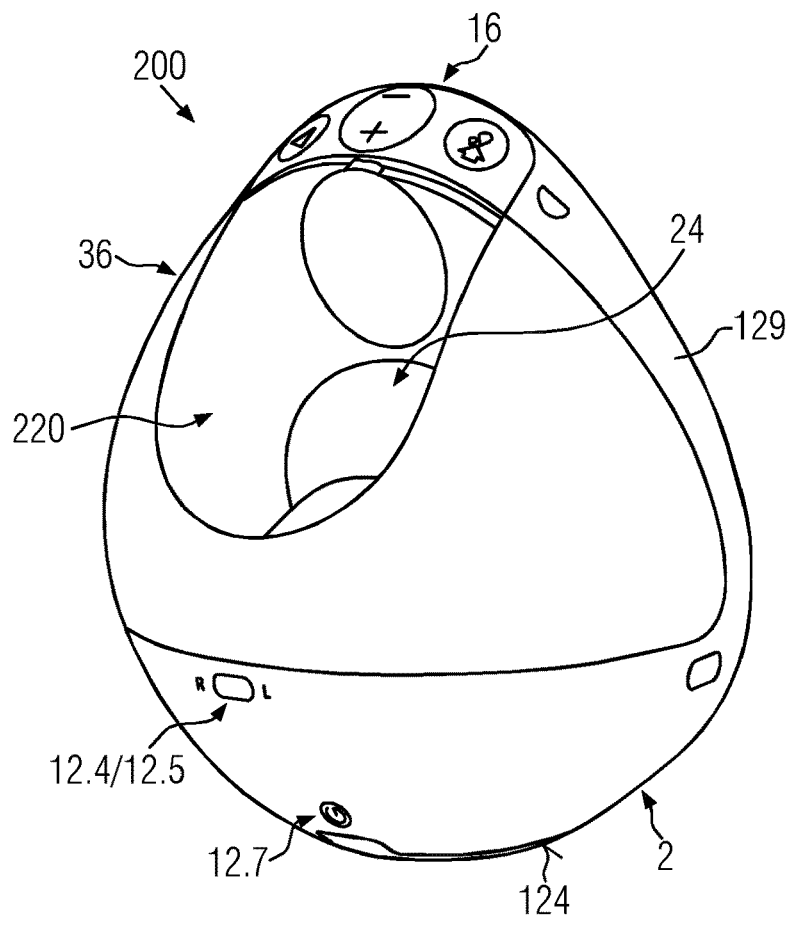
FIG. 10
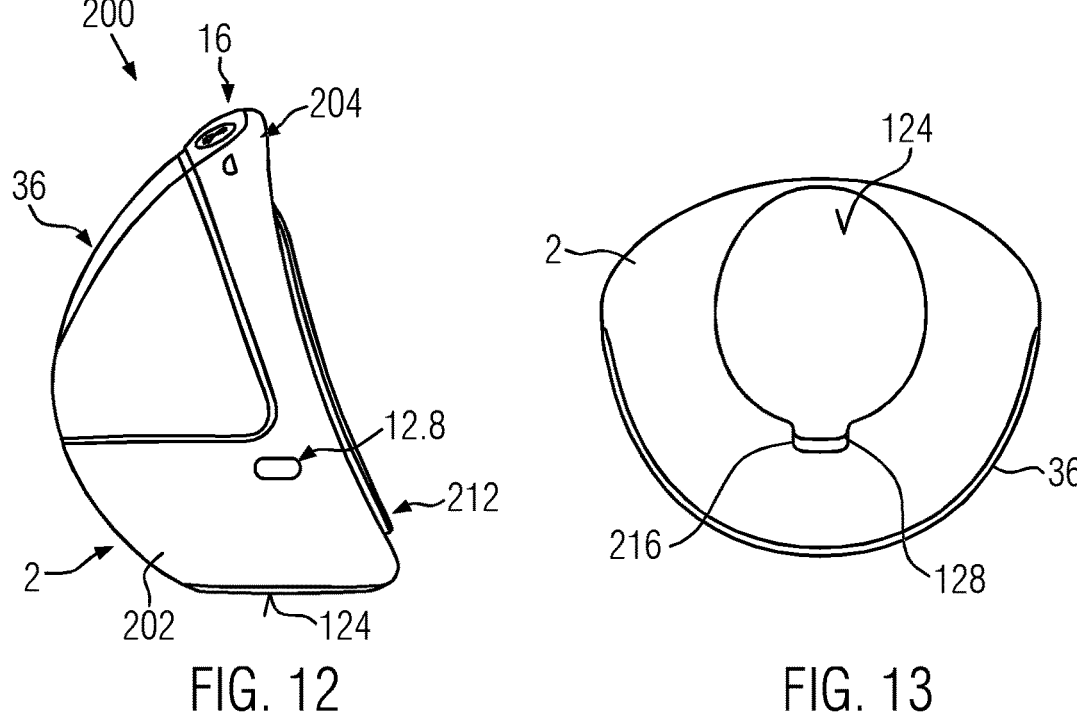
FIG. 12                 FIG. 13

BREAST PUMP AND METHOD FOR OPERATING SUCH PUMP

CROSS-REFERENCE TO RELATED APPLICATION

This present application is the US national phase of International Patent Application No. PCT/EP2022/067266, filed Jun. 23, 2022, which claims priority to European Application No. 21181505.5, filed Jun. 24, 2021. The priority application, EP 21181505.5, is hereby incorporated by reference in its entirety.

FIELD OF THE DISCLOSURE

The present invention relates to a breast pump shaped at least in part to fit inside a bra. The breast pump comprises a housing and a breast shield element. The breast shield element includes a nipple tunnel adapted to receive a nipple. The breast pump furthermore has a rigid milk container adapted to contain a predetermined amount of expressed milk. Inside the housing, an aggregate is received, which aggregate provides the power for generating a suction pressure for expressing milk of a breast-feeding mother.

In-bra breast pumps are known from, e.g., WO 2018/ 229504 A1. This breast pump has a semi-spherical housing. The housing shell being convex on the front and adapted to lay against the bra whereas the backside of the housing is concave and provides a receptacle for insertion of the breast shield element and the nipple tunnel thereof. The bottom of the housing is flat for attaching a rigid milk container, which is snapped against the housing. The breast shield element is likewise secured against the housing by snapping. In use, the nipple tunnel is received within the housing. The breast shield element is made of a transparent material to allow confirmation of proper nipple alignment. The breast shield element projects beyond the bottom of the housing. The milk container provides a flat base surface adapted to support the breast pump in an upright position.

The breast shield element of the breast pump known from WO 2018/229504 A1 provides a cup-shaped pumping chamber housing adapted to be connected at its outer ring with a membrane element, which membrane element will be sandwiched between the breast shield element and the housing after inserting the breast shield element into the housing. The milk container has an opening which is releasably closed by a separate cap element, which cap element is projected by a tube adapted to receive a valve element made of a soft elastomeric material adapted to sealingly cooperate with a nipple tunnel formed by the breast shield element to surround an outlet port formed at a circumference of the nipple tunnel.

The aggregate described in WO 2018/229504 A1 is an air pump which is fed by air, located within the housing, and generates a negative pressure within the housing, which cyclic pressure is transferred to a chamber closed off by a membrane element, which membrane element separates an air duct communicating with the air pump form a duct formed by the breast shield and in fluid communication with the nipple tunnel.

This prior art breast pump has several disadvantages. It is of rather bulky design. Furthermore, proper alignment of the nipple within the nipple tunnel can only be effected with the breast shield element being dismounted from the housing in a cumbersome, two-handed manner, involving placement of the breast shield onto the breast, rotation of the breast shield around the nipple inserted into the nipple tunnel, and only after the breast shied is held in place on the breast with the nipple received in the nipple tunnel, the housing is then slid onto the breast shield and latched to the housing. Furthermore, in use, the user cannot observe milk flow during pumping operation as the milk container is arranged below the housing. This arrangement also prevents the user from detecting the amount of expressed milk contained within the milk container. Further, correct fluid connection between the nipple tunnel and the milk container requires precise positioning of the breast shield element and the milk container relative to the housing and proper fastening of the breast shield element to the housing and fastening of the milk container to the housing.

This pump has the further disadvantage that it leaks in case of rather small deviations from the vertical position of the pump, i.e., when the pump is leaning forward. In this prior art pump, a venting hole is provided at a top of the milk container, which milk container is provided below the housing. Thus when using the pump with the user standing or sitting, the interface between the housing and the milk container extends essentially in a horizontal plane, which horizontal plane likewise comprises the venting hole.

The further disadvantage is the fact that the membrane element is arranged above the nipple tunnel in use. Moreover, a membrane working chamber is in direct fluid communication with the nipple tunnel without a valve being interdisposed therebetween. The membrane working chamber is sealed by the membrane element and arranged opposite to a working side of the membrane element, which opposite side is used to drive the membrane for the pumping action. As the membrane element is arranged above the nipple tunnel, air is a predominant component within the membrane working chamber and the nipple tunnel during pumping.

A further breast pump system is known from U.S. Pat. No. 8,702,646 B2. This breast pump system comprises an outer shell element and a breast shield element with a nipple tunnel. The prior art breast pump furthermore has a media separation element, which is attached to an inner closed end of the nipple tunnel, thereby sealingly surrounding an outlet port provided at a circumference of the nipple tunnel. A lower end of the media separation element is connected to a valve element leading to a milk compartment surrounded by the outer shell element. The upper end of the media separation element is adapted to connect to a hose leading to an external vacuum source, which hose has to be inserted into an insertion hole at an outer circumference of the outer shell element.

EP 3 777 911 A1 discloses a breast pump having an outer shell element adapted to be connected to a pump module which sits on the outer periphery of the outer shell element. The housing surrounds a media separation element adapted to be connected to a valve element at its lower end and to a membrane element at its upper end. This media separation element is adapted to be secured to an inner close end of a nipple tunnel provided by a breast shield element. This breast shield element provides a closure of the housing.

WO 2017/139437 A1 discloses a breast pump and a method for operating the same. In this prior art breast pump, the nipple tunnel is connected with a pumping chamber, which pumping chamber is in communication with a milk container. Between the pumping chamber and the milk container a container valve is provided which prevents reflux of expressed milk from the milk container towards the pumping chamber. This container valve is a typical one-way valve which is activated by the pressure difference between the pumping chamber and the pressure in the milk chamber surrounded by the milk container. Between the milk chamber and the nipple tunnel, there is provided an actuated valve. The actuated valve comprises two compression members which sandwich a flexible hose and squeeze the hose inbetween in order to close the conduit formed by the hose between the nipple tunnel and the pumping chamber. During expansion of the pumping chamber leading to an increased negative pressure, the actuated valve is opened to allow milk to be drawn from the nipple tunnel into the pumping chamber. In case of a compression, the actuated valve is closed in order to avoid reflux of the milk into the nipple tunnel while forcing the milk through the container valve into the milk chamber.

Due to this constitution, the prior art breast pump is a fluid-filled pump. In contrast to WO 2018/229504 A1, in which the air pump predominantly air fills the nipple tunnel during pumping operation, the nipple tunnel and the pumping chamber are constantly filled with milk. Thus, disadvantages of the compressible medium air are avoided. There is a rather direct transmission of the pumping strokes of the pump into the nipple tunnel. Moreover, the wet conditions within the pump correspond to the natural environment of a breast feeding mother.

SUMMARY OF THE DISCLOSURE

It is an object of the present invention to provide a breast pump which at least partially avoids the disadvantages discussed with respect to WO 2018/229504 A1.

As a solution to this problem, the present invention provides a breast pump shaped at least in part to fit inside a bra and comprising a housing including an aggregate, a breast shield element including a nipple tunnel adapted to receive a nipple and a rigid milk container adapted to contain a predetermined amount of expressed milk. The breast shield element and the milk container are detachable from each other and removable from the housing. For this and according to one aspect of the present invention, the breast shield element may be connected/attached to the milk container.

One aspect of the present invention provides the advantage that the parts leading from the nipple tunnel into the milk container are directly connected with each other. Thus, correct spatial arrangement of those parts is facilitated to the fact that the breast shield element is connected to the milk container. The connection between the breast shield element and the milk container can be embodied as any releasable connection.

On a regular basis, the nipple tunnel of the breast shield element comprises the means for connecting the breast shield element to the milk container. The connection usually is a direct connection or attachment. In other words, a physical link is provided usually between the nipple tunnel, most preferably an end region of the nipple tunnel and the milk container. In particular, the milk container and the breast shield element may comprise mating surfaces of a bayonet or a threaded (screw-like) connection. On a regular basis, the housing is sandwiched between a flange of the breast shield element and the milk container. This means, that the housing is received between the breast shield, in particular the flange of the breast shield element which is adapted to connect to the breast of the feeding mother, and the milk container. Due to this constitution the housing may be prevented from moving relative to the breast shield element and/or the milk container in longitudinal direction of the nipple tunnel.

The aggregate provides a driving force for expressing milk. The aggregate may be a motor which is coupled to a membrane being wetted by the expressed milk. The aggregate may provide suction pressure inside or outside the housing or at an interface between the housing and the milk container. Most preferably, the aggregate drives a piston, which piston may be coupled mechanically to the motor. The piston moves the membrane. Preferably, the membrane may follow the movement of the piston. For, this the piston may be coupled with the membrane; specifically, the membrane may contact the piston.

A sealed volume between the membrane and the piston may couple the membrane and the piston in such a way, that the membrane follows the reciprocating movement of the piston. The sealed volume may contain air as a cushion between the piston and the membrane, which cushion transmits the reciprocating movement of the piston onto the membrane. The amount of air in the sealed volume may be reduced such that the piston at least partially contacts the membrane. The seal of the volume may be adapted to allow air to be forced out of the sealed volume as the piston is advanced towards the membrane while not allowing air to enter the sealed volume as the piston moved in the reversed direction. As a result, a vacuum will build up within the sealed volume and the membrane will abut against a drive end side of the piston.

Preferably, the membrane moves with the piston. Most preferably, the piston and the membrane move with the same frequency.

The membrane may be sandwiched between the housing and the milk container and may be releasably secured to the milk container and/or the housing. The sealed volume may be sandwiched between the housing and the milk container. A housing bellows may be provided between the membrane and the motor, in particular between the membrane and a drive end side of the piston, which a drive end side may be provided by a cap section of the piston. The housing bellows may be arranged essentially flush with an outer surface of the housing.

According to another aspect of the present invention, the piston is in contact with the membrane. Thus, the driving activity or energy of the aggregate is directly transferred to the membrane thereby providing exact volume changes of a pumping chamber when expanding or reducing the same. In prior art WO 2018/229504 A1 an air pump drives the membrane through compressible air. Accordingly, the movement of the membrane cannot be exactly controlled.

The membrane preferably is sandwiched between the housing and the milk container and defines at least in part the pumping chamber, which pumping chamber may be defined between walls of the nipple tunnel and walls of the milk container. According to one further aspect of the present invention, the membrane is provided opposite to the piston. A clamp space is defined between the membrane and the piston. This clamp space is adapted to allow trapped air to be driven out of clamp space as the piston reciprocates. Such air may be contained in the clamp space as a result of assembling the pump, thereby laying the membrane against or at least adjacent to the housing. The clamp space will prevent ambient air from entering into the clamp space as the piston pulls the membrane towards the housing to expand the pumping chamber. In other words, after commencement of pumping, a vacuum seal is provided within the clamp space between the membrane and the piston, which vacuum seal couples the membrane with the piston. Thus, the membrane usually follows the movement of the piston.

Preferably, the housing at least in part circumferentially surrounds the nipple tunnel in radial direction of the nipple tunnel. The housing can be U-shaped or V-shaped. Preferably, the housing may have a central bore through which the nipple tunnel projects. Thus, the housing is securely held in place as the breast shield element is connected to the nipple tunnel protrudes through the housing and at least in part through the milk container. Accordingly, the nipple tunnel at least in part projects through the housing. The housing preferably is ring-shaped. A ring shaped housing does not necessarily have to have a cross-sectional geometry like a geometric ring. The ring-shaped housing is ring-shaped as it has a bore, which bore is fully surrounded by a material of the housing in circumferential direction. Sandwiching the housing between the flange of the breast shield element and the milk container with the nipple tunnel projecting through a bore of the housing is suitable to essentially maintain the housing in place without attaching the housing to either the flange of the breast shield or the milk container. Nevertheless, the housing may as well in addition or per se be secured to the flange and/or to the nipple tunnel. In case the nipple tunnel projects through a bore of the housing, alignment means may be provided between the flange and the housing and/or between the housing and the milk container in order to secure a specific orientation of the breast shield and the housing and/or the milk container and the housing. In other words, the housing will be prevented from rotating around the longitudinal axis of the nipple tunnel to assume an indefinite spatial relationship to the nipple tunnel and/or the housing.

Nevertheless, it should be emphasized that the housing can be directly connected to the breast shield, in particular the flange thereof and/or the milk container to provide a milk pump constituted of joined components even if the housing does not have a bore being projected by the nipple tunnel. The connection between the housing and the breast shield or the milk container usually is a releasable, preferably a mechanical connection using a force fit, friction fit, interference fit, and/or a positive fit.

For connecting the breast shield element to the milk container, the milk container usually has a nipple tunnel receptacle adapted to receive at least a forward end of the nipple tunnel. In a side view, the housing preferably is wedge-shaped. Thus, the lower portion of the housing is thicker than the upper portion of the housing. Such wedge shape will improve visibility of the nipple within the breast shield. Such wedge shape will allow to arrange spacious or heavy components like a rechargeable battery and/or a motor for driving a membrane in a lower part of the housing. The center of gravity of the pump relative to a longitudinal axis of the nipple tunnel can be adjusted by appropriately arranging the components within the housing. The center of gravity of the pump relative to a longitudinal axis of the nipple tunnel should be below, above or on the longitudinal axis of the nipple tunnel when holding the pump in correct upright orientation with the longitudinal axis of the nipple tunnel extending horizontally. In order to be in conformity with the shape of the breasts and the flange of the breast shield element, the housing has a concave rear surface, which concave rear surface at least in part corresponds with the geometry of the breast shield element, in particular the flange thereof. The surface opposite to the rear surface, i.e. the front surface of the housing preferably is flat i.e. essentially planar. Alternatively, it may be slightly curved in a convex or concave fashion. The same is true for the rear surface of the milk container. This rear surface usually has a mating geometry conforming with the geometry of the housing for a compact design. This constitution is to allow rotational movement of the milk container relative to the housing after the nipple tunnel has been inserted into a nipple tunnel receptacle provided by the milk container.

This nipple tunnel receptacle is usually provided to extend into the milk container. The constitution will allow to deliver expressed milk into a milk chamber usually through a container valve connected to the nipple tunnel receptacle and adapted to open and close a milk path which is surrounded by the nipple tunnel receptacle.

This nipple tunnel receptacle usually provides securing elements like threads or projections cooperating with mating threads or projections on the outer circumference of the nipple tunnel to releasably secure the breast shield element against the milk container. When being connected to the nipple tunnel receptacle, an annular milk path is usually provided circumferentially around the nipple tunnel, i.e. between the outer circumferential surface of the nipple tunnel, in particular only the front end of the nipple tunnel and the inner circumferential surface of the nipple tunnel receptacle. This constitution has proven to improve pumping performance and efficiently drawing of expressed milk from the nipple tunnel in the direction of the milk container. The annular milk path is usually directly connected with or forms part of a pumping chamber provided with a membrane, which membrane is driven by the aggregate received within the housing.

The aforementioned nipple tunnel receptacle usually forms part of a lid element of the milk container, which lid element is adapted to sealingly close a container shell element. Preferably, the lid element, most preferably the tunnel receptacle also is adapted to sealingly receive the breast shield, specifically the nipple tunnel. As the milk container provides the forward end of the inventive breast pump when being used as the user is standing or sitting, the container shell element preferably is spherical.

In an upright position, the longitudinal axis of the nipple tunnel essentially extends in vertical direction. Respective upright position of the device is usually supported by the center of gravity of the breast pump, e.g. when the milk container is empty. This center of gravity secures the position in which the breast pump rests on the milk container. In this position, the milk container is the lowest component followed by the housing, which housing is sandwiched at least between the milk container and the flange of the breast shield element. The center of gravity of the breast pump preferably is in accordance with the above in any filling stage of the milk container i.e. full, half full or empty.

The spherical container shell element may cover the entire front of the breast pump. Thus, a fairly large amount of expressed milk can be collected within the milk container, i.e. between the spherical container shell element and the lid element. The lid element may be detachably secured against the spherical container shell element. The lid element detached from the milk container may still engage the milk container e.g. by a living hinge or the like. Preferably, one of the container shell element or the lid element is provided with a container seal made of a soft elastomeric material. This seal is usually connected to at least one of the shell element or the lid element, which are preferably made of a hard plastic material, by injection molding the soft elastomeric material like a TPE around the lid element and/or the shell element. The seal may alternatively be formed as a separate component and may permanently or releasably be secured to the lid element or the shell element. The seal may be made of silicone.

For mechanically securing the lid element against the shell element, both elements usually provide a hinge, which hinge allows a swiveling movement of the lid element relative to the shell element. The hinge is a releasable hinge connection. Thus, the lid element and the shell element can be completely disengaged by disengaging mating hinge elements of the lid element and the shell element, respectively. Alternatively, the container shell element and the lid element may be inseparable, e.g. be connected by a living hinge or the like joining the two components in the event they are not coupled to form the milk chamber.

Opposite to the hinge, the lid element is usually provided with a spout adapted to pour expressed milk out of the milk container after use of the pump. In the use position, the spout assumes the highest point of milk container and the pump is used by a user sitting or standing. For closing the spout, the lid element preferably holds a spout closure element. This spout closure element is movably held by the lid element. Usually, the spout closure element is slidable relative to the lid element and adapted to assume at least three positions. In a securing position, the spout closure element secures the lid element against the container shell element. In a removal position, in which the spout closure element is shifted inwardly, removal of the lid element from the container shell element is possible. For this the lid element will usually be pivoted about the hinge and finally be detached from the container shell element. The spout closure element furthermore is adapted to assume a position intermediate of the securing position and the removal position. This intermediate position is a pouring position, in which the lid element no longer close the spout provided between the lid element and the container shell element. Thus, in the pouring position, expressed milk can be poured out of the milk container. However, the spout closure element will still secure the lid element against the container shell element in the pouring position. Accordingly, expressed milk collected in the milk container can be poured out of the milk container while keeping the lid element in place and the milk chamber within the milk container securely sealed. As the milk container per se can be sealed by the spout closure element, it will be capable of storing expressed milk for a longer time without deteriorating the quality of the expressed milk. Nevertheless, in the securing position the lid element shall still allow venting of the milk chamber while still closing the same to avoid spill of milk.

The milk container preferably has a front section arranged in longitudinal extension of the longitudinal axis of the nipple tunnel, which corresponds to the longitudinal extension of the nipple tunnel receptacle. This front section preferably has a flat support section to allow stable support of the milk container on a flat surface. Opposite to said flat support surface the milk container has the spout provided at a generally flat rear surface. The flat support surface is arranged such that the spout assumes the highest point of the milk container being supported on a horizontal plane by means of the flat support surface.

In order to allow venting of the milk container when pumping expressed milk into the milk container, the milk container preferably comprises a milk container venting valve. This milk container venting valve can be an active or a passive venting valve. The milk container venting valve usually has a soft elastomeric valve element which cooperates with a surface of the milk container. A passive milk container venting valve will vent the milk container due to a pressure difference. In other words, the passive milk container venting valve will open for venting the milk container in case of a threshold pressure within the milk chamber, which threshold pressure is higher than the atmospheric pressure surrounding the breast pump during use. The active milk container venting valve is activated by a milk container venting valve actuator to control venting valve activity. Such milk container venting valve actuator may open the milk container venting valve dependent on a pressure difference, which pressure difference is the difference in pressure within the milk chamber and the atmospheric pressure. The milk container venting valve actuator may also open the milk container venting valve dependent on elapsed time after commencement of pumping and/or last milk container venting valve operation. The milk container venting valve actuator may be formed by any suitable actuator. Specifically, a Piezo drive may control venting valve operation.

In order to properly control suction pressure within the nipple tunnel, the present invention proposes a two-way valve interdisposed between a free end of the nipple tunnel and a portion of the milk container, which milk container portion is usually provided by the closed end of the nipple tunnel receptacle. The two-way valve element comprises a milk outlet valve cooperating with the nipple tunnel to allow expressed milk to be drawn from the nipple tunnel into the milk container under a predetermined suction pressure. The two-way valve element furthermore comprises a reflux valve cooperating with the milk container to allow control of the suction pressure within the nipple tunnel and will prevent an excessive negative pressure within the nipple tunnel. The reflux valve will allow milk to flow back from a pumping chamber into the nipple tunnel to decrease the negative pressure within the nipple tunnel up to 20 mmHg. Thus, the negative pressure within the nipple tunnel will not be higher than a base line vacuum of 20 mmHg. Accordingly, the two-way valve element may likewise be regarded to comprise a base line valve element.

Cooperation of the two-way valve element with the nipple tunnel and the milk container is usually such that the milk outlet valve is closed due to abutment of the valve element against a wall section of the nipple tunnel. In case of a suction pressure, the two-way valve element will be elastically deformed away from the nipple tunnel thereby opening the milk outlet valve to allow expressed milk to be drawn from the nipple tunnel towards the milk container as a consequence of an increasing volume within the pumping chamber. An adverse movement is made by the two-way valve element in case of an excessive negative pressure within the nipple tunnel to open the reflux valve which is usually closed by abutment against the milk container and as the volume of the pumping chamber decreases. Preferably, the nipple tunnel receptacle of the milk container has a projection which protrudes into the milk path and has a flat closing surface contacting the two-way valve or at least the reflux valve of the two-way valve and thereby closing the reflux valve under usual pressure conditions whereas the two-way valve element is bent towards the nipple tunnel and thus lifted from the closing surface to open the venting valve.

In the above-described embodiment, the breast pump preferably has three chambers which are in fluid connection with each other and separated by valves. The first chamber i.e. the nipple chamber is provided by the nipple tunnel and the remaining volume between the front end of the nipple tunnel and the breast at least partially received in the nipple tunnel and/or projecting into the nipple tunnel. The third chamber is the milk container. The second chamber is the pumping chamber provided between the nipple chamber and the milk chamber. Expressed milk is transferred from the nipple tunnel to the pumping chamber and from the pumping chamber into the milk container. Valves direct the flow and prevent to some extent reflux of the milk. The volume of the pumping chamber changes due to the movement of a membrane element driven by the aggregate. The reflux valve may allow reflux of milk from the pumping chamber into the nipple chamber.

In operation, the breast pump, by varying the volume of the pumping chamber, provides a pressure within the nipple tunnel of between −300 mmHg and −20 mmHg, thereby maintaining the latch between the breast and the breast shield. As the volume of the pumping chamber increases, the reflux valve cannot move as the sealing force around it grows due to rising vacuum inside the pumping chamber as the pumping chamber expands. The maximum vacuum inside the nipple tunnel is defined by the volume the pumping chamber may expand to. The reflux valve plays a role when the pumping chamber contracts. Then, pressure inside the pumping chamber grows opening the reflux valve so the pressure inside the nipple tunnel increases, closing the milk outlet valve and opening the container valve allowing milk transfer to the container. The resistance of the reflux valve will not allow the pressure inside the nipple tunnel to increase to atmospheric pressure leaving −20 mmHg. At −20 mmHg the adverse movement of the reflux valve occurs closing the reflux valve. The only valve that remains open is the container valve as in the minimum volume at the end of pumping chamber contraction the pressure inside the pumping chamber goes slightly above atmospheric pressure, forcing the milk valve to open or to stay open.

As mentioned above, the nipple tunnel preferably is essentially cylindrical with a round cross-sectional surface. Preferably the nipple tunnel receptacle is likewise essentially cylindrical with a round cross-sectional area. This constitution allows to screw-connect the nipple tunnel within the nipple tunnel receptacle. This constitution will lead to an annular milk path having essentially the same thickness in circumferential direction. Respective milk path is in fluid connection with a pumping chamber and usually forms part of the pumping chamber. This pumping chamber is usually at least in part provided between a rigid wall of the milk container, preferably provided by the lid element of the milk container and a membrane element. This membrane element is usually releasably held between the milk container and the housing. In fact, the membrane is usually sandwiched between the milk container and the housing and thus sealed in between those two components.

Threads of a screw or bayonet connection between the breast shield element and the milk container are usually sealed against the annular milk path. Thus, the threads arranged outside of the pumping chamber do not fully circumferentially surround the nipple tunnel and/or the nipple tunnel receptacle. Instead, plural individual threads are provided spaced apart from one another in circumferential direction. The threads will usually provide sufficient mechanical connection as a result of an overall rotational movement between the milk container and the breast shield of between 40° and 100°, preferably as a result of a rotational movement of between 50° and 70°. The housing and the milk container are preferably provided with mating positive fit means like a projection and a mating recess receiving the projection to avoid rotational movement between the housing and the milk container.

According to a preferred embodiment of the present invention, the above-mentioned pumping chamber is defined between the nipple chamber and the milk chamber. Between the pumping chamber and the nipple tunnel, there are provided a milk outlet valve and a reflux valve. The milk outlet valve is adapted to allow expressed milk to be drawn from the nipple tunnel into the pumping chamber. The reflux valve will allow reflux of milk from the pumping chamber into the nipple tunnel. Between the pumping chamber and the milk chamber, there is provided a container valve adapted to allow milk flow from the pumping chamber into the milk chamber. The milk outlet valve, the reflux valve and the container valve usually are each activated by pressure difference, only, which pressure difference is the difference of the pressure inside the pumping chamber and the milk chamber, respectively. In other words and contrary to prior art WO 2017/139437 A1, an actuator for driving at least one valve is dispensable.

As already mentioned above, the reflux valve is designed to allow reflux of milk until a reduced threshold suction pressure is present in the nipple tunnel. This reduced threshold suction pressure is usually about 20 mm Hg negative pressure. Due to the pumping activity of the aggregate, a high threshold suction pressure can exist in the nipple tunnel, which high threshold suction pressure is in the range of 250 mm Hg to 300 mm Hg negative pressure.

In case of an expansion, the pressure within the pumping chamber will increase. The reflux valve will open to allow milk to enter into the milk channel until the reduced threshold suction pressure is reached. Upon a pressure reducing action of the aggregate, the pressure within the pumping chamber will be reduced. Thus, the reflux valve is closed while the milk outlet valve will open to draw milk from the nipple tunnel into the pumping chamber. The container valve as a one-way valve is closed to avoid reflux of milk from the milk chamber into the pumping chamber.

The milk thus collected in the pumping chamber will leave the pumping chamber upon the next expansion activity of the aggregate. On a regular basis, the pumping chamber is completely filled with milk. Therefore, the amount of milk expressed in one pumping cycle will completely be advanced into the milk chamber in the next pumping cycle. The reflux valve will maintain the reduced threshold suction pressure and will likewise secure a wet ambient of the nipple received within the nipple tunnel.

This aspect can be an individual aspect of the present invention, which may form part of a separate individual invention. For this invention to be realized, it is not necessary that the breast shield is directly connected to the milk container. Moreover, the housing does not necessarily have to have any air pump or aggregate received therein. The pump may be an external pump. For this separate aspect of the present invention, the milk outlet valve and the reflux valve do not necessarily have to be provided by a single two-way valve element, which is mentioned above. Instead, each of the valves can be formed by a separate valve element, which valve element is usually made of a soft elastomeric material.

In case of such a two-way valve element, respective valve element preferably provides an outer seal sealing the pumping chamber against the outer circumference of the nipple tunnel and/or the nipple tunnel receptacle. Thus, the annular milk path is restricted to the forward end of the nipple tunnel.

According to a parallel aspect, the inventive breast pump allows partial detachment of at least one element from at least another element of the breast pump, which other element is still held within the bra. Irrespective of the way of connecting the different elements of the breast pump, the same comprises at least a milk container, a breast shield element, and a housing, which housing does not necessarily have to include an aggregate but may comprise such aggregate. If the aggregate is not contained within the housing, the same provides an interface for an external suction source.

According to this parallel aspect, an angular gap is provided between the housing and the breast shield element or the milk container and adapted to receive a portion of the bra. Accordingly, the bra is sandwiched in between at least two elements of the inventive breast pump. The annular gap does not have to be provided fully extending in circumferential direction around the nipple tunnel or nipple tunnel receptacle. On a regular basis, the gap is provided between the rear end of the breast shield element, i.e. the flange and a free end of the nipple tunnel. The gap may extend essentially perpendicular to the longitudinal axis of the nipple tunnel. The annular gap may be slightly inclined relative to said longitudinal axis of the nipple tunnel. In a side view of the breast pump in use, the annular gap may be inclined not more than 30°, preferably not more than 20°, relative to an axis perpendicular to the longitudinal axis of the nipple tunnel. The annular gap is preferably inclined towards the head of the user. In other words, the upper portion of the annular gap is directed towards the rear surface of the breast pump. Thus, the upper end of the annular gap has a smaller distance to the rear surface of the breast pump than the lower end of the gap. The size of the gap, i.e. the thickness of the annular gap preferably is between 0.1 and 5 mm. Such size of gap will allow the usual textile materials of the bra to be received within the annular gap. In case the gap is provided between the housing and the milk container, the milk container can be placed outside of the bra. Thus, the breast shield and the housing can be kept in place inside the bra while a milk container may be taken away and e.g. replaced by an empty milk container. Thus, there is no need to completely remove the pump from the bra after filling up a single milk container.

The inventive breast pump preferably has means for monitoring milk flow and/or pumping performance including proper alignment of the nipple within the nipple tunnel. A camera can for example be integrated into the breast pump, preferably within the housing, which camera may be connected to a mobile device like a mobile phone to allow visual monitoring via the screen of the handheld device/ mobile phone. The breast pump can for example integrate a sensor as described in EP 3 373 997 B1, WO 2019/145163 A1 or WO 2018/210685 A1. The camera mentioned above is preferably received within the housing. The camera shall be adapted to observe at least a portion of the nipple tunnel, which portion is essential for checking proper nipple alignment within the nipple tunnel and/or checking milk flow through or out of the nipple tunnel.

The inventive pump may have a fill sensor monitoring the level of fluid within the milk container, which sensor may likewise detect movement or a high fluid level due to an inappropriate orientation of the milk pump during pumping as e.g. the user of the pump may lean forward. Such incident may be noted by comparing the regular yields of milk during said pumping section. In the event that measured fill level of milk within the milk container does not match with the expected level, the control of the pump may conclude inappropriate orientation or an excessive level of movement and may pause the aggregate such, that baseline vacuum is maintained but further milk is not drawn from the breast of the user. In case the fill sensor detects the pump to assume an appropriate orientation and/or a lesser degree of movement by detecting lower fill level within the milk container, the control may order the aggregate to commence pumping activity. With such constitution, any additional sensor detecting potential spill of milk within the milk container can be avoided. Moreover, as the spout is arranged at the upper most end of the milk container and as the milk container essentially fully extends in vertical direction of the pump when being used with the user sitting or standing orientation, spill of milk within the milk container due to a high level of movement or inclination is not an issue.

For visually controlling the conditions within the nipple tunnel, the nipple tunnel and/or the milk container are at least partially made of a transparent material to allow the user to visually check proper nipple alignment of the nipple within the nipple tunnel or milk flow. In addition, the housing may at least be partially made of a transparent material or comprise a window which allows monitoring nipple alignment and/or milk flow in a use position, in which the pump is laid against the breast of the user. Such transparent portion of the housing or the milk container is usually aligned with elements of a user interface. Those elements of the user interface are preferably mounted on a peripheral portion of a housing directed towards the face of the user when using the breast pump. Thus, elements of the user interface, as well as the actual conditions within the nipple tunnel, can be monitored visually by the user during use.

In order to allow such visual control at night, the breast pump preferably has at least one light source received within the housing and adapted to illuminate at least one element of the user interface or an optical indicator provided on the housing. This optical indicator may indicate electric energy conditions of a battery received within the housing or critical filling condition of the milk container. In order to avoid scatter of the light emitted by the light source, there preferably is provided a light guide element adapted to focus light emitted from the light source on an icon of the user interface or the optical indicator. Preferably, a light guide element is provided for each icon and each indicator. Thus, the icons or optical indicators are illuminated in a focused way, thereby avoiding light disturbance which could illuminate the environment which may be disadvantageous when using the breast pump at night. The light guide element may be formed by a glass fiber element. Multiple light guide elements may be assigned to a single light source in order to focus the light emitted from the light source to plural icons and/or optical indictors of the user interface.

This light source or an additional light source may be provided usually within the housing and adapted to direct a light beam on the nipple tunnel. At least one light source may be directed towards the nipple tunnel and arranged in radial direction thereof. Such light source could be arranged underneath the nipple tunnel, i.e. below the longitudinal axis in the field of gravity when using the pump sitting or standing. Alternatively or in addition, the at least one light source may be arranged in a front surface of the housing and directed towards the milk container.

Thus, if the nipple tunnel and the milk container are at least partially made of a transparent material, visual inspection of the conditions within the nipple tunnel can be carried out in the dark/at night. As previously mentioned and for avoiding scattered light for this embodiment, the light beam of the respective light source is focused on the nipple tunnel. For visually checking pumping condition and/or nipple alignment, the present invention proposes to make the nipple tunnel and a nipple tunnel receptacle of the milk container at least partially of a transparent material. The nipple tunnel receptacle and/or the nipple tunnel are provided with at least one optical mark. The optical mark may be guide lines indicating proper positioning of the nipple within the nipple tunnel. The optical mark may be a pattern which extends in axial and circumferential direction of the nipple tunnel and covers just a portion thereof. The pattern has a different optical quality than the transparent material of the nipple tunnel and the nipple tunnel receptacle. Instead of markings, a light beam may be directed towards the nipple tunnel to provide a light guide for proper nipple alignment and/or selection of a proper sized breast shield. Such light beam may be a beam of white or colored light and projected onto the breast shield element or the milk container. In such an embodiment, the nipple tunnel will be visible through transparent portions of the housing and/or the milk container and/or the breast shield. Those transparent portions in the use position of the breast pump arranged between the eyes of the user and the nipple tunnel. For proper selection of breast shield size, the light beam may project a light array onto the nipple tunnel assigning the proportions thereof to the breast received within the breast shield.

The breast shield element and/or the milk container and/or the housing are at least partially made of a transparent material, visual inspection of the conditions within the nipple tunnel can be carried out in the dark/at night. Moreover, any transparent part or portion of the breast pump may be used as the light guide by introducing light into the element which light is guided through the respective element or portion and may illuminate portions and/or at least one guides and/or at least one user interface. Decoupling of the light out of the light guide may be obtained by frosting the transparent material and/or by providing one or more mirrors, which are usually formed when injection molding the respective element or portion.

Any transparent material used for at least in part making the pump may have changing optical properties dependent on the angle of incident light and/or view in order to e.g. shield the breast form being viewed from outside by an unauthorized person. The transparent material may have the properties of a privacy filter allowing just the user to look into the nipple tunnel along the optical axis of the user. The transparent properties may be modifiable by the application of electricity and/or heat. The transparent material may be a thermochromic and/or an electrochromic material.

Transparent in the meaning of the present invention shall be considered as a quality of the material allowing a clear view through the material or a frosted transparent quality allowing visibility to a lesser extent but still sufficient to e.g. check proper position of the nipple within the nipple tunnel and/or milk flow or amount of expressed milk within the milk container. The pattern may be frosted transparent on a crystal clear transparent material or may be opaque on a crystal clear transparent material or a frosted transparent material. The pattern is usually provided on a top section of the nipple tunnel or nipple tunnel receptacle. The pattern usually has a size adapted to cover a residual volume of air which cannot fully be excluded during pumping operation of the pump. This residual air rests above the milk within the nipple tunnel. The size of the residual air within the nipple tunnel is an indicator for proper nipple alignment and/or pumping performance. The pattern is such that it covers the volume of residual air within the nipple tunnel at good or optimal pumping conditions. In other words, if the pattern fully covers the residual air, the user is confirmed of optimum pumping conditions and/or nipple alignment whereas air within the nipple tunnel extending beyond the pattern will visually indicate improvable pumping conditions, thus, motivating the user to adjust the pump.

The breast pump preferably has a sensor determining the amount of expressed milk within the milk container. This sensor may monitor milk flow and count/or volume of expressed milk, e.g. when being delivered into the milk container. The sensor may optically or inductively measure the level of fluid within the milk container. This sensor may employ any technique known in prior art in combination with breast pumps for monitoring amount of expressed milk within the milk container. The sensor is coupled with a control processing the sensor signal to conclude amount of expressed air within the milk container. The control is also assigned to an indicator indicating a filled up condition of the milk container. This indicator is usually an icon provided within the interface, which icon preferably is illuminated as described above.

According to a preferred embodiment, the aggregate includes an electric motor drivingly coupled with a reciprocating drive as generally known from WO 2019/080995 A1, which prior art describes a gear to transform rotational movement of the motor into a reciprocating linear movement of a membrane by screw-nut-gear. Alternatively, a pinion and rack gear may be provided. The drive member preferably is a longish element in the form of a spindle or rod, which is connected to a bellows sealed against the housing. This housing bellows is operatively coupled to the aggregate. This housing bellows avoids contamination to reach the aggregate inside the housing. The piston is reciprocating in a working space provided within the housing. The housing bellows is usually coupled to a free end or drive end side of the piston and is also connected to and sealed by the housing at a rim of a working space of the piston. This housing bellows is preferably covered with the membrane, which membrane at least in part defines the pumping chamber. During operation, the membrane is usually wetted by the expressed milk. During operation, the housing bellows will not come into contact with the milk within the pumping chamber. Usually, the membrane is arranged between the pumping chamber and the housing bellows. The drive member may be a brushless motor or a coreless motor. The drive member may be built directly on a PCB or a chip. In such a case, the PCB serves as a mechanical base and takes the function of the housing in a standard motor. The drive member may include a pulley drive. The shaft of the drive member may be provided co-axially with the longitudinal extension of the spindle or rod being connected to the housing bellows.

In a preferred embodiment, which can be assembled economically, the housing bellows is sandwiched between the housing and a drive housing. The drive housing is the element of the drive which supports either the gear or the gear and the electric motor or the motor, only.

From the above description it is evident, that the pump of the inventive breast pump usually is not received within the housing as taught by WO 2018/229504 A1. Preferably, the housing contains the aggregate, only, which aggregate is usually a motor driving a piston in a reciprocating motion. The piston is an example for a reciprocating drive means of the present invention. Preferably, this reciprocating motion is directly transferred to a membrane closing a working chamber. The working chamber is usually sandwiched between the housing and the milk container, specifically between the housing and the lid of the milk container. The movement of the membrane cyclically varies the volume of the working chamber and thus expands and reduces the volume of the pumping chamber.

The above-mentioned membrane protects the piston from being directly wetted by the milk. Thus, respective membrane is usually constituted by a separate independent membrane element, which is releasably attached to the milk container, specifically to the lid thereof. The membrane may be secured to the milk container in any suitable way e.g. magnetically or adhesively. Preferably, the piston is provided with a housing bellows, which is sealed within the housing. The membrane usually is positioned between the housing bellows and the container lid. When placing the housing against the milk container in the course of assembling the breast pump, the membrane may contact the housing bellows. At least when commencing pumping by reciprocating the piston, residual air between the housing bellows and the membrane will be expelled from the space between the housing bellows and the membrane. As a consequence, a vacuum seal will form within said space through which the membrane contacts the piston and/or the housing bellows connected to the piston. By reciprocating the piston, milk is drawn into the membrane working chamber and expelled therefrom as the piston will expand and reduce the volume of the membrane working chamber. The aforementioned valves, at least the container valve and the milk outlet valve will cooperate with the reciprocating movement of the piston to direct milk from the nipple tunnel into the milk container. Accordingly, the essential components for initiating and directing the milk flow from the nipple tunnel into the milk container are provided outside of the housing, which contains only the motor for reciprocating the piston but no means for directing a fluid flow.

Specifically, the inventive breast pump can be considered, when fully assembled, to comprise an internal pump for providing a directed flow of milk within the breast pump. This internal pump comprises at least two valves for directing the milk flow and the membrane element for driving the milk by direct contact with the milk. Those two valves and said membrane element are received in the milk container; i.e. are surrounded or covered at least in by the milk container. While the membrane element is attached to an outer surface of the milk container, it is predominately received within the membrane working chamber defined by the milk container, i.e. the lid element thereof and thus received in the milk container. Arrangement of one of the valves on a front free end of the nipple tunnel, which nipple tunnel is received with a nipple tunnel receptacle formed by the milk container, will likewise render this valve to be received in the milk container. In any event, the at least two valves for directing the milk flow and the membrane element for driving the milk are not contained in the housing.

Moreover and as mentioned above, the reciprocating movement of the piston will not cooperate with a compressible medium like air as e.g. taught in WO 2018/229504 A1. Instead, the reciprocating movement of the piston may directly be transferred via the vacuum seal to the membrane element which is wetted by the milk and thus cooperates with an incompressible fluid. Due to this, the milk is actively drawn from the nipple tunnel and effectively transferred into the milk container when reducing the volume within the membrane working chamber. Thus, pumping is more effective than in the solution of WO 2018/229504 A1 which utilizes a compressible air to be introduced into a membrane working chamber, which membrane working chamber in said prior art is separated from the milk side by the membrane.

According to a further preferred embodiment, the breast pump of the present invention has a sheet element comprising an opening adapted to receive the nipple tunnel and to be sandwiched between the milk container and the housing. Respective sheet element radially projects at least one of the milk container and the housing. The sheet element can be made of any suitable material like metal, plastic or paper/cardboard. The sheet element can help the user to become familiar with the use of the pump. Thus, the sheet element may contain information how to assemble or disassemble the breast pump, in particular how to unscrew and thus release the breast shield element from the milk container. Information in this respect is in particular provided on the free end of the sheet element which radially projects the milk container or the housing. Respective information is usually provided by an arrow indicating the rotational movement, e.g. of the milk container relative to the housing and/or breast shield element for detaching the milk container. In addition, the sheet element may be provided with a QR code or the like directing the user to a manual accessible via internet.

According to a further aspect of the present invention, the housing of the inventive breast pump defines a circumferential rim adjacent to a rear surface of the housing, which rear surface usually provides an abutment surface for the flange of the nipple breast shield. In fact, the rear surface and the circumferential rim merge into each other at approximately a right angle. Along the circumferential rim elements of a user interface are provided such that the elements of the user interface are visible for the user when the nipple tunnel is received within the nipple tunnel and the breast pump is proper alignment with the body of the user. For this to achieve, the spout is usually arranged to be the or near the highest point of the breast pump as the user is sitting upright or standing.

According to a yet further aspect of the present invention, the same provides a method for operating a pump. In said method, and as the breast is laid against the breast shield, a nipple chamber is defined between the breast and the free end of the nipple tunnel. Via a milk outlet valve, this nipple chamber is in fluid communication with a pumping chamber. Via a container valve, the pumping chamber is in fluid communication with a milk chamber defined by the milk container.

In the inventive method, and at commencement of pumping, air is sucked out of the nipple chamber while expressed milk flows from the breast into the nipple chamber. The air is released from the milk container and further expressed milk will fill the fluid path between the nipple chamber and the milk valve and this the entire pumping chamber. Milk will build a hydraulic coupling between the breast and the membrane. Thus, movement of the membrane will be hydraulically transmitted to the breast inside the nipple tunnel. This means, that any movement of the membrane will essentially be directly transferred and without any loss in activity or intensity to the breast. For this to achieve, small air bubbles may still be contained within the hydraulic column between the membrane and the breast.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth. As used herein "(s)" following a noun could mean the plural and/or singular forms of the noun.

Further details, advantages or features of the present invention will become apparent from the following description of a specific embodiment in combination with the drawings. In the drawings:

BRIEF DESCRIPTION OF THE SEVERAL
VIEWS OF THE DRAWING

FIG. 4 is a rear view of the first embodiment;

FIG. 5 is a front view of the first embodiment;

Figures 9A, 9B, 9C:
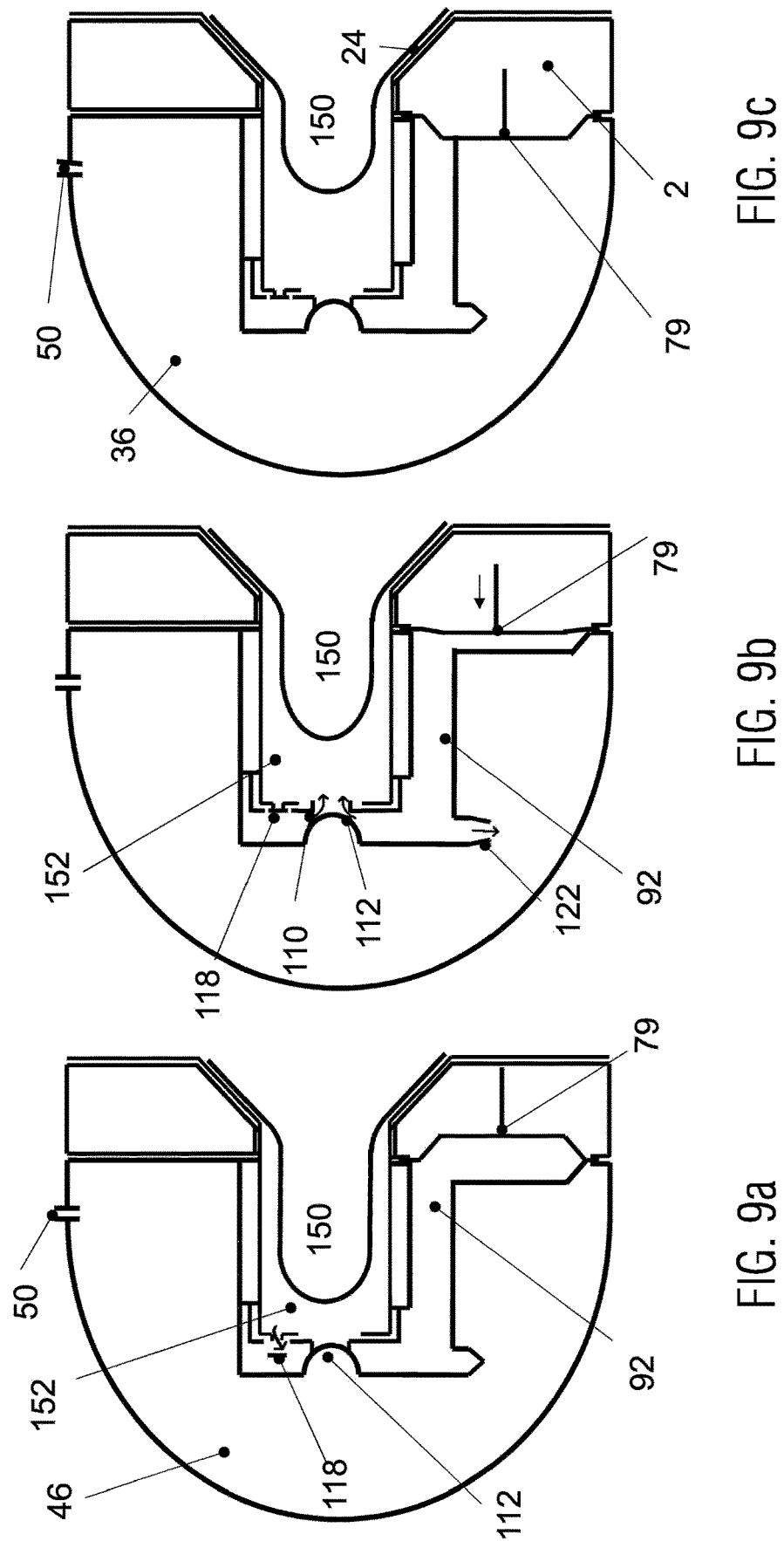
FIG. 9*a* is a schematic side view elucidating the pumping performance for a fully expanded pumping chamber.
Figure 11:
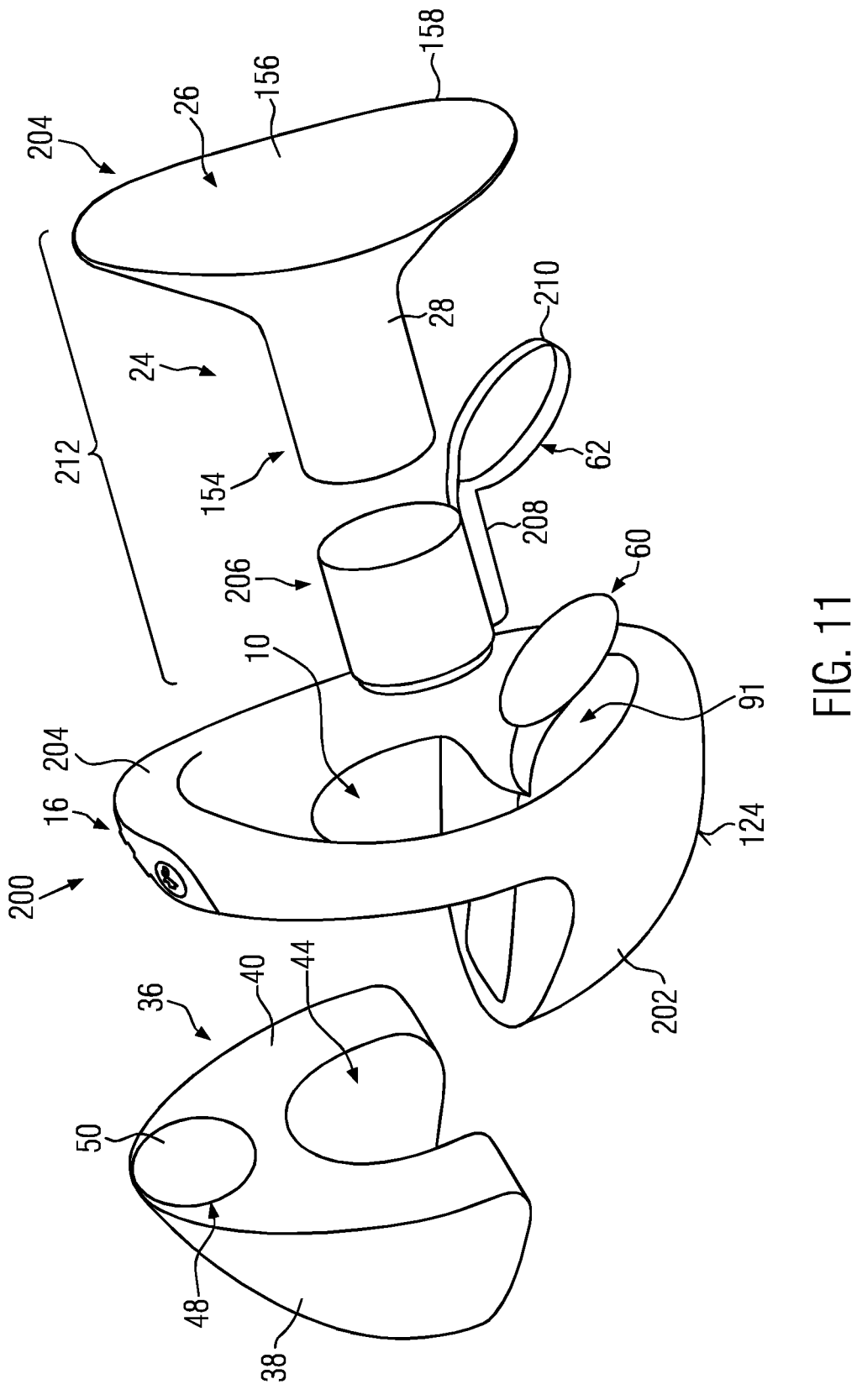
Figure 14:
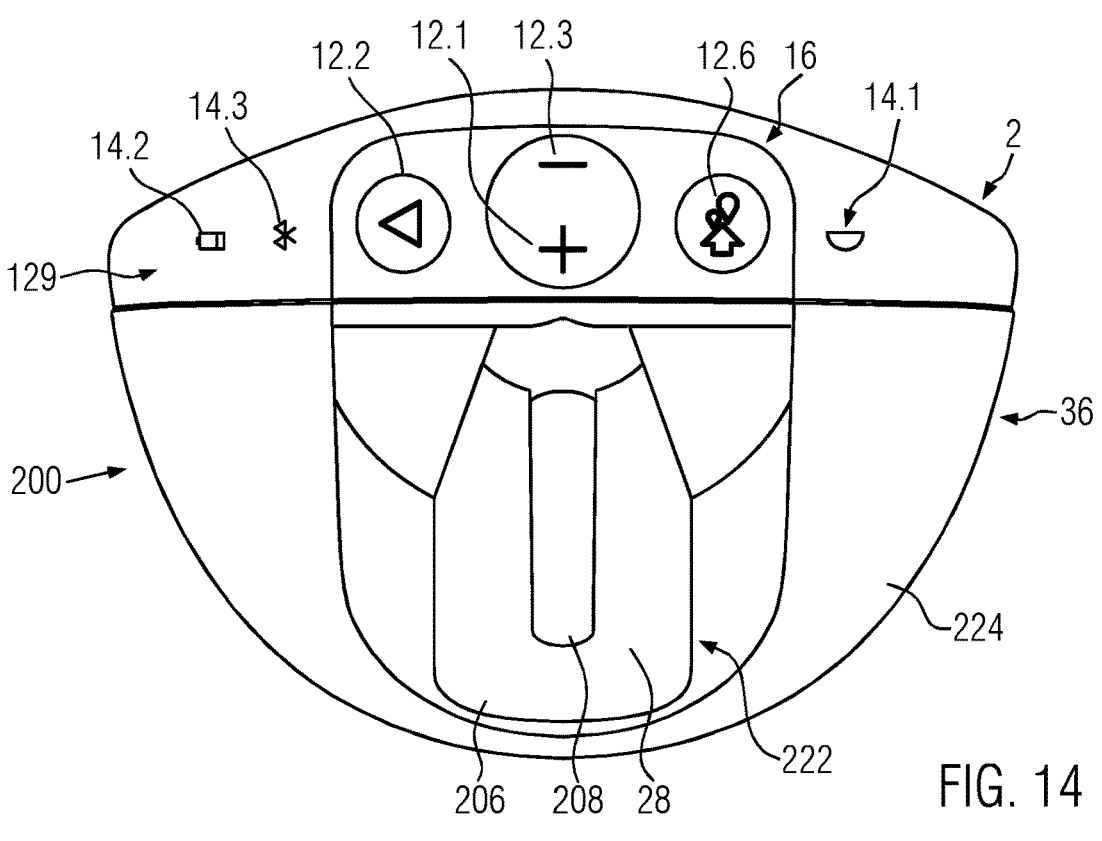
Figure 15:
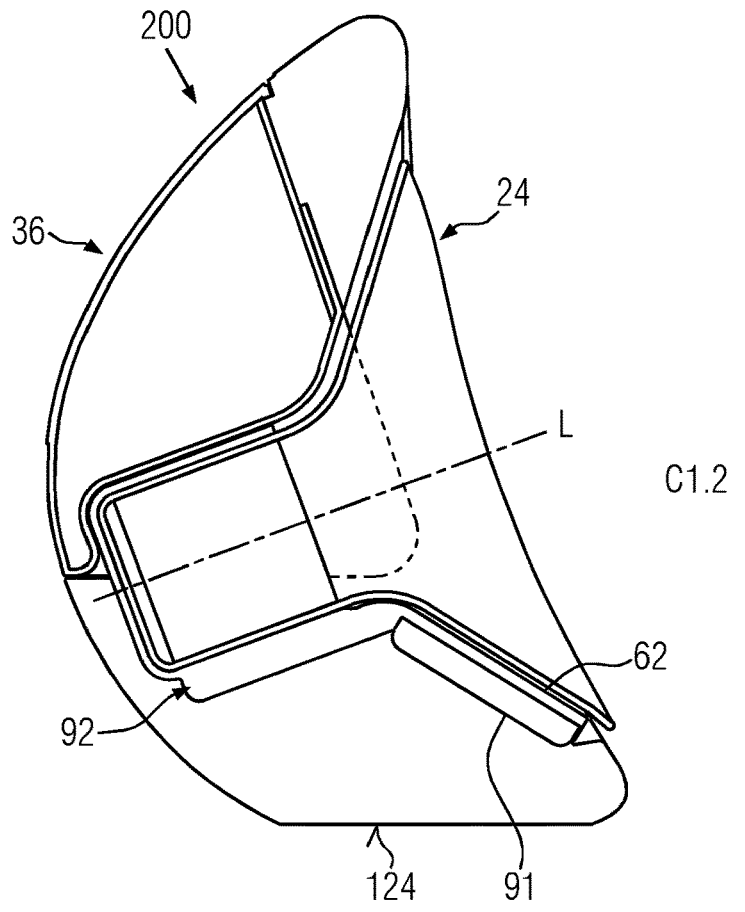
Figure 16:
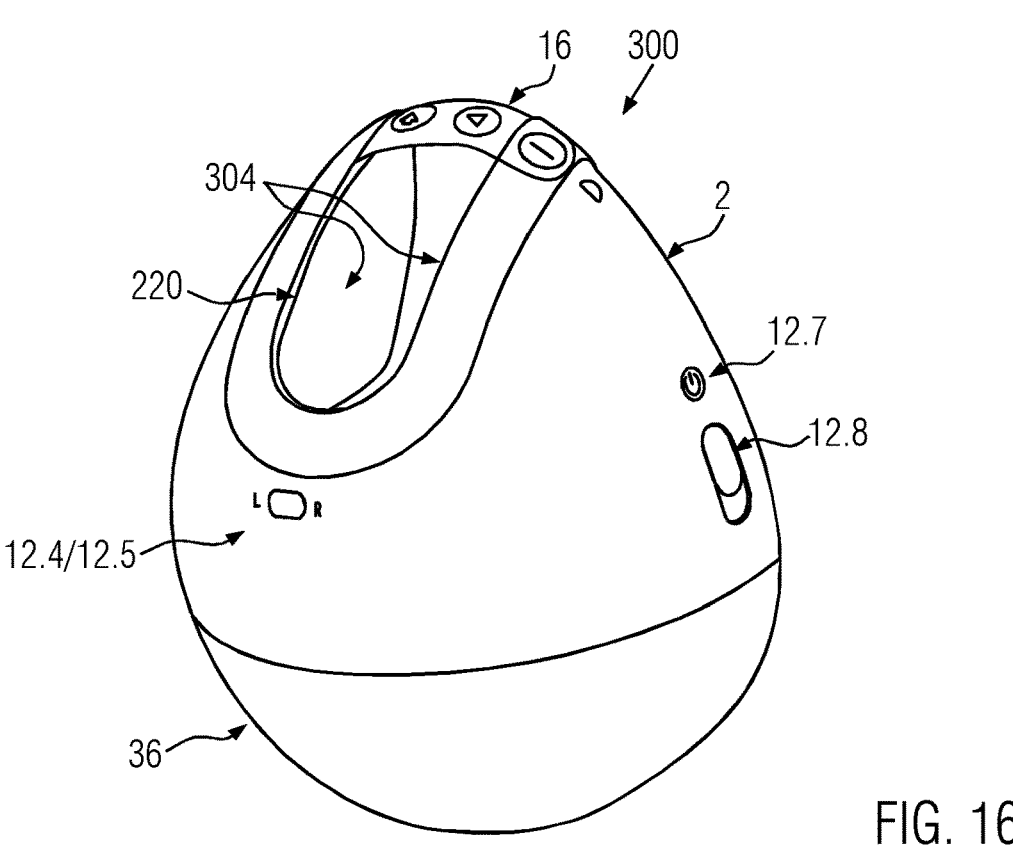
Figure 18:
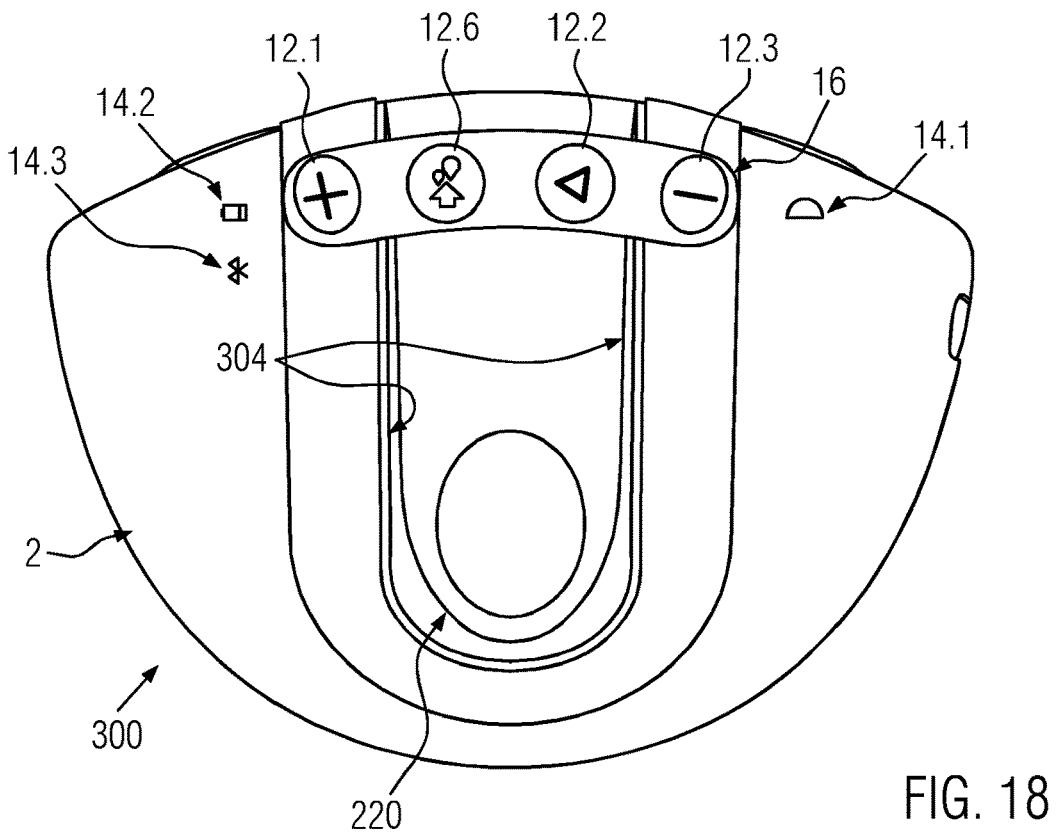
Figure 17:
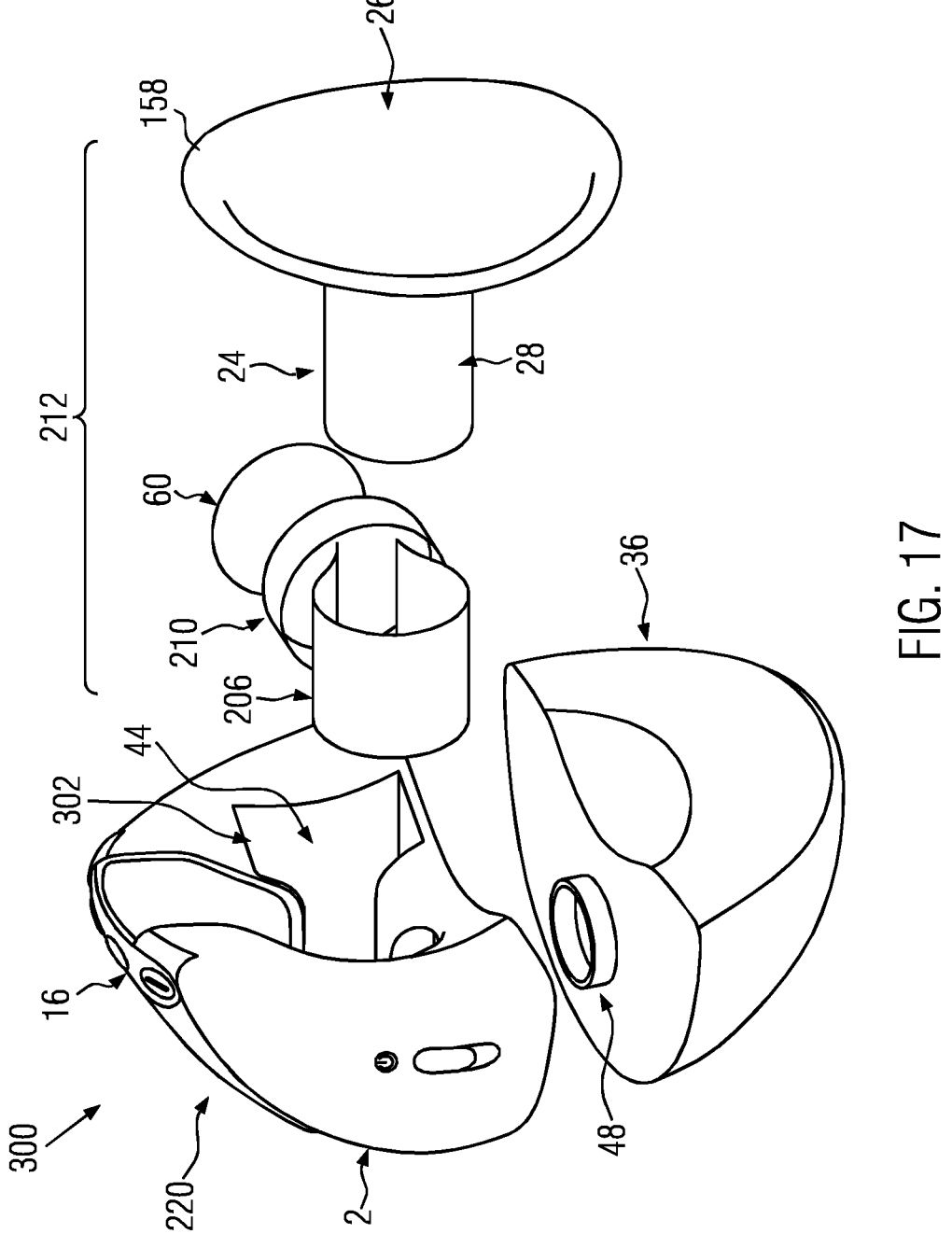
Figure 19:
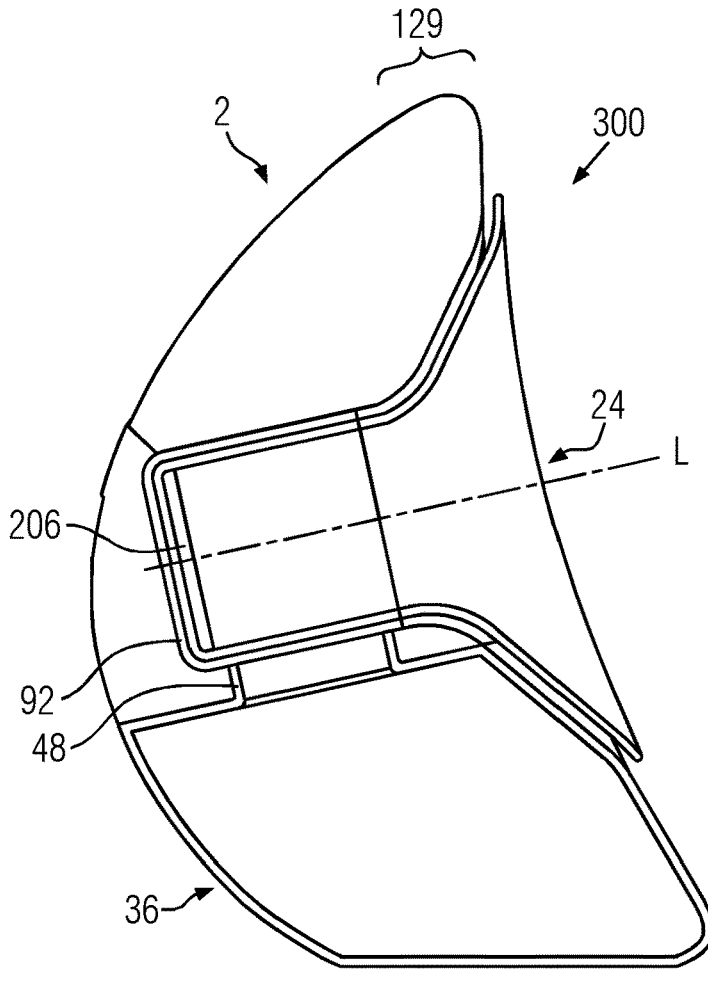
Figure 20:
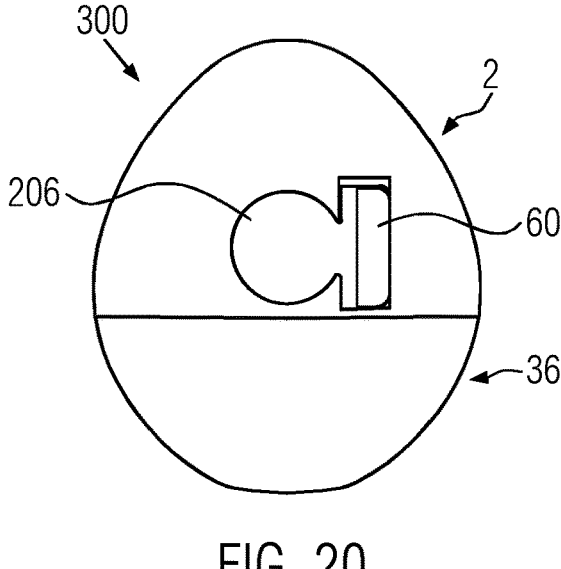
Figures 21, 23:
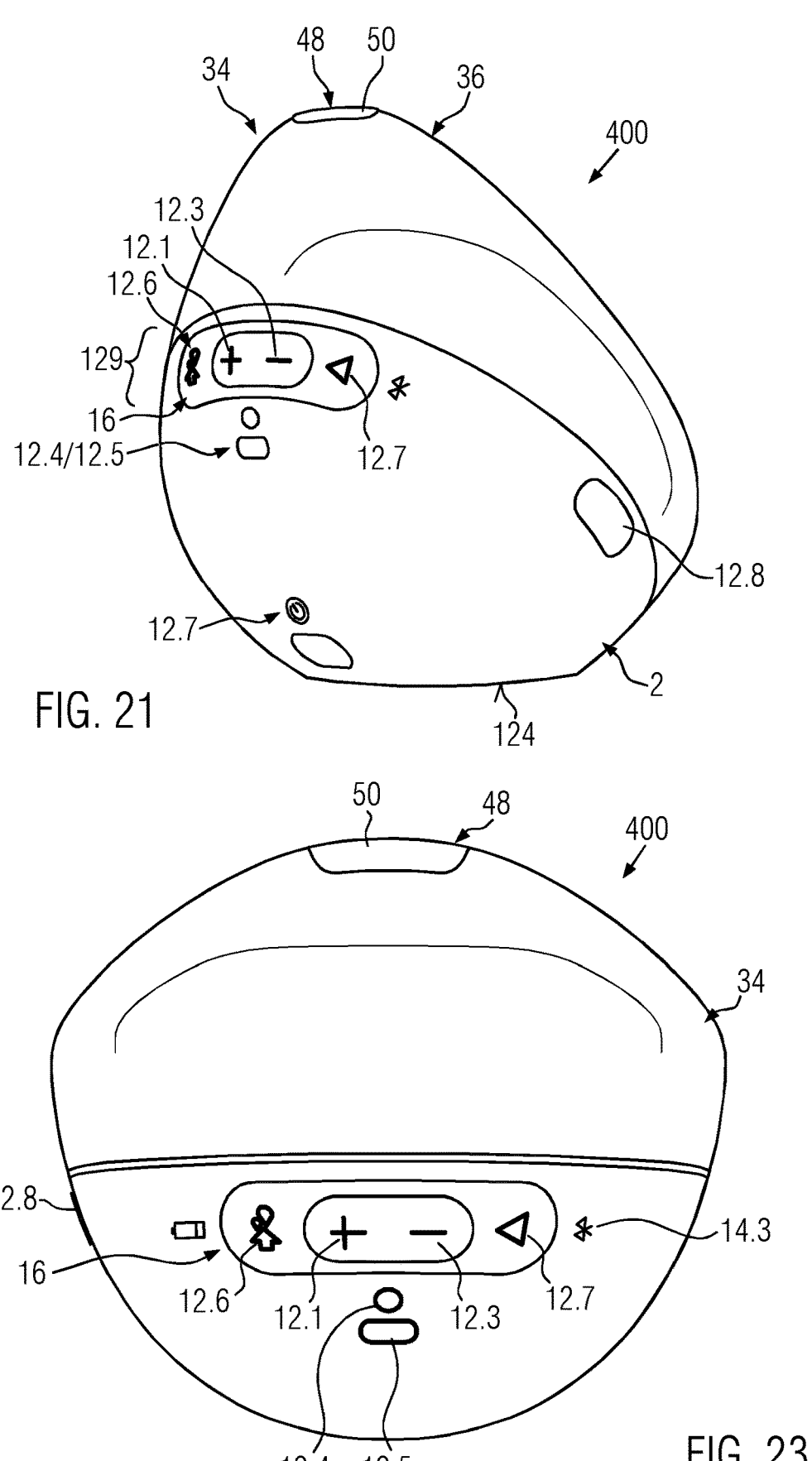
Figures 22, 24:
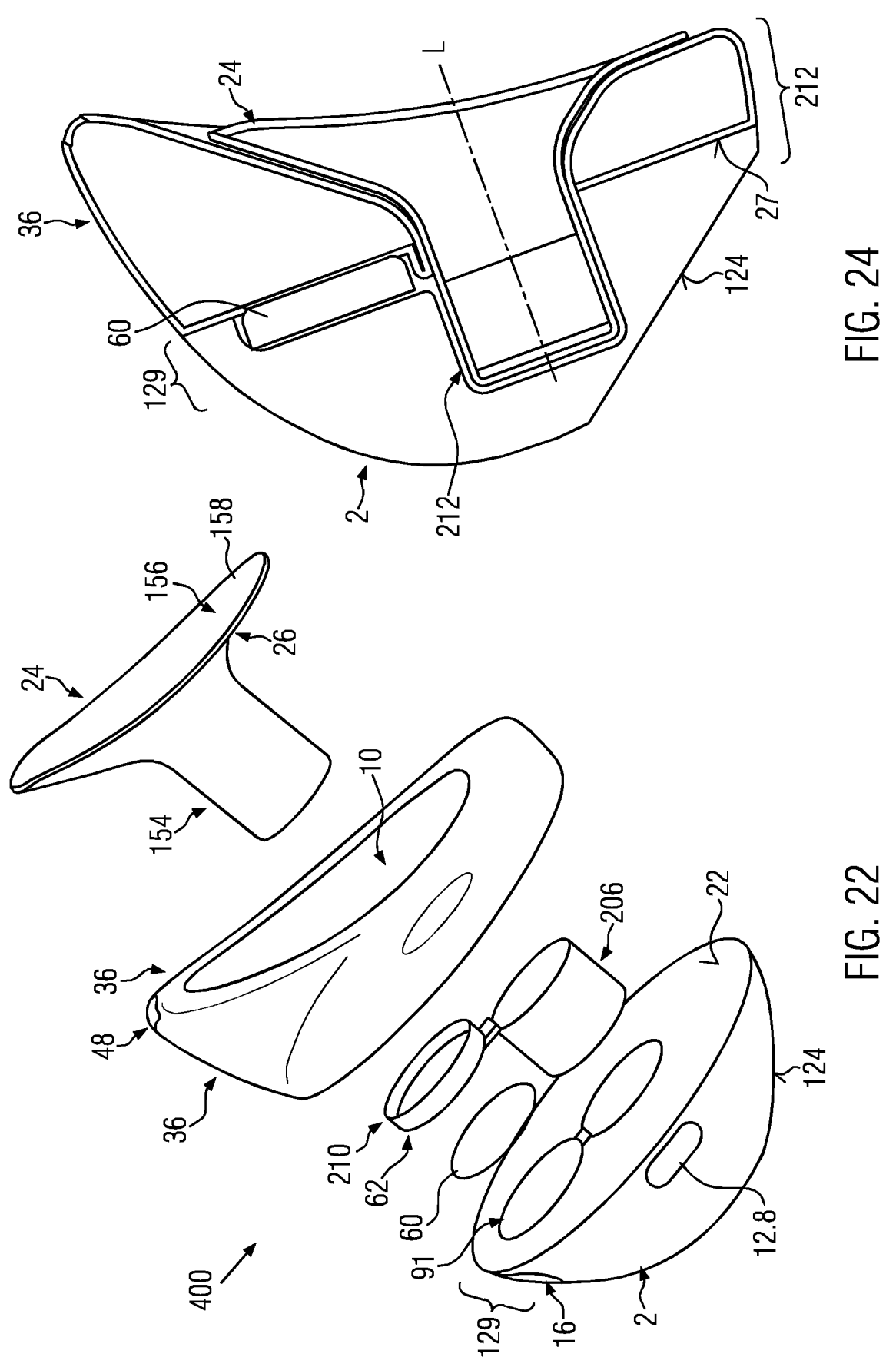

FIG. 9*b* is a schematic side view elucidating the pumping performance for a pumping chamber during contraction;

FIG. 9*c* is a schematic side view elucidating the pumping performance for a fully contracted pumping chamber;

FIG. 10 is a perspective front view of a second embodiment according to the present invention;

FIG. 11 is an exploded view of the individual components and elements of the second embodiment;

FIG. 12 is a side view of the second embodiment;

FIG. 13 is a bottom view of the second embodiment;

FIG. 14 is a top view of the second embodiment;

FIG. 15 is a schematic sectional view of the second embodiment in longitudinal direction;

FIG. 16 is a perspective front view of a third embodiment according to the present invention;

FIG. 17 is an exploded view of the individual components and elements of the third embodiment;

FIG. 18 is a top view of the third embodiment;

FIG. 19 is a schematic sectional view of the third embodiment in longitudinal direction;

FIG. 20 is a schematic cross-sectional view of the third embodiment;

FIG. 21 is a perspective front view of a fourth embodiment according to the present invention;

FIG. 22 is an exploded view of the individual components and elements of the fourth embodiment;

FIG. 23 is a top view of the fourth embodiment and

FIG. 24 is a schematic sectional view of the fourth embodiment in longitudinal direction.

DETAILED DESCRIPTION OF THE PREFERRED EMBODIMENTS

Figure 1:
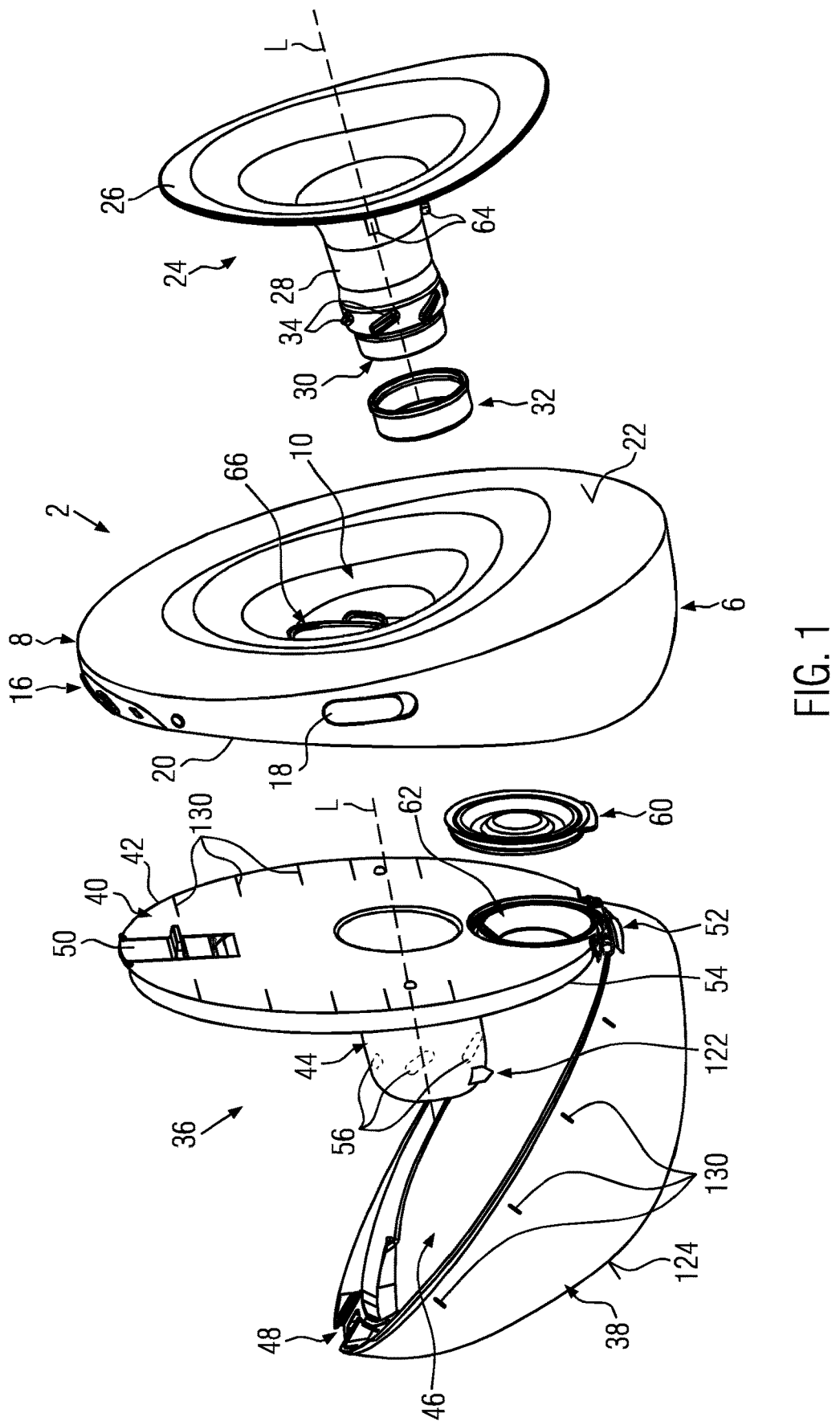
FIG. 1 is an exploded view of the individual components and elements of a first embodiment of the breast pump according to the present invention.
Figure 2:
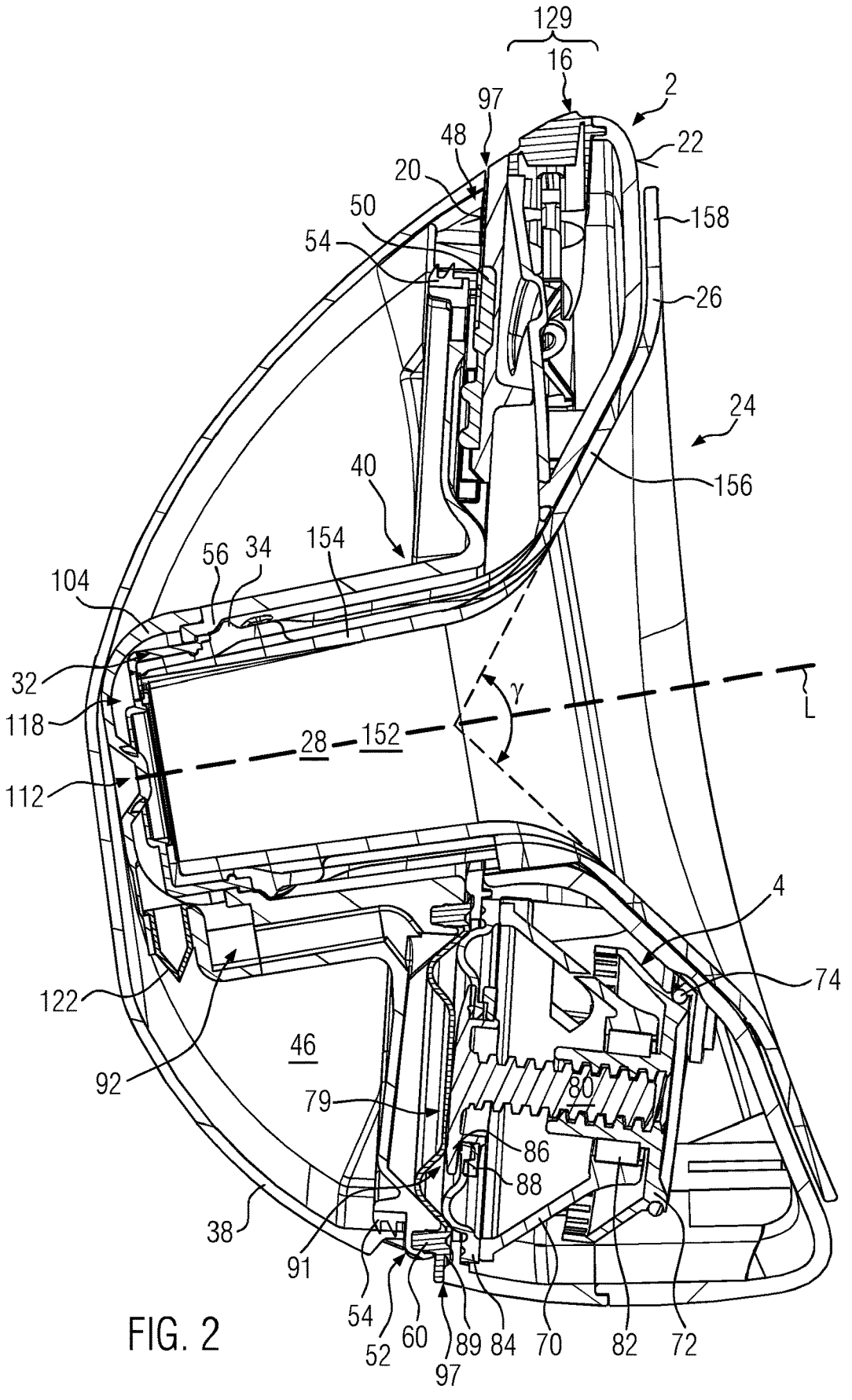
FIG. 2 is a cross-sectional view of the first embodiment in an assembled state.

In FIG. 1, reference numeral 2 identifies a housing including an aggregate 4 (compare FIG. 2). The housing 2 is made of opaque plastic material. In a side view, the housing is wedge-shaped. A bottom section 6 of the housing 2 is considerably thicker than the top section 8 of the housing 2. In a front or rear view, the housing is essentially avocado-shaped or round. The largest width of the housing 2 is essentially level with a longitudinal axis L, which longitudinal axis defines a bore 10 (compare FIG. 4). The housing 2 circumferentially encloses this bore 10. Accordingly, the housing 2 is ring-shaped.

Figure 6:
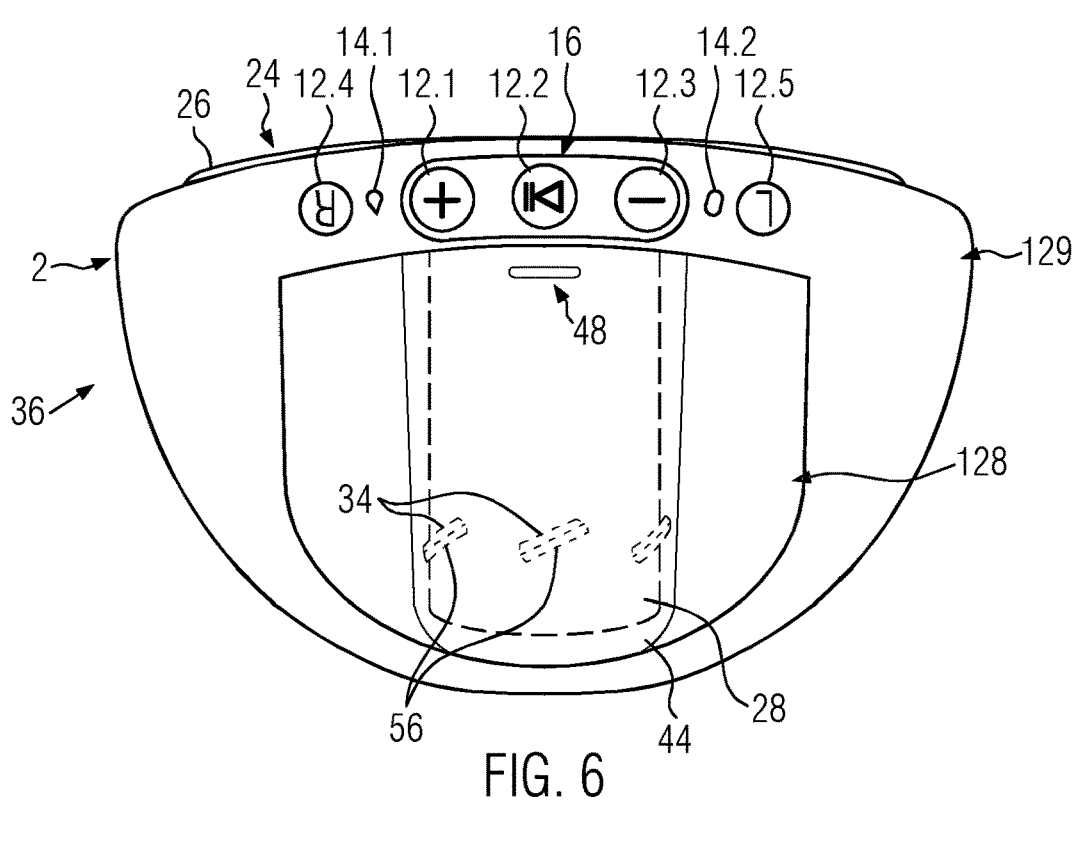
FIG. 6 is a top view of the first embodiment.

The circumference of the top section 8 is provided with elements 12 of a user interface 16 and optical indicators 14 indicating operational information of the pump. Details of the elements 12 and the optical indicators 14 are derivable from FIG. 6. Reference numeral 12.1 is an element of the user interface 16, which element 12.1 will be used to increase the pumping suction pressure, whereas element 12.3 will lower the pumping suction pressure. Element 12.2 can be used to either pause or activate the aggregate 4.

Optical indicator 14.1 provides information of the amount of expressed milk within a milk container. Accordingly, this optical indicator 14.1 indicates a filled up status of a milk container. Indicator 14.2 indicates the charge status of an internal electric supply like a battery or an accumulator. Elements 12.4 and 12.5 are buttons to switch between the use of the pump for the left L and the right R for log statistics to assign yield of expressed milk to each of the breasts.

In FIG. 1, reference numeral 18 identifies a cover allowing access to a USB plug.

As derivable from FIG. 1, a front surface 20 of the housing 2 is flat, whereas a rear surface 22 of the housing 2 is concave.

In FIG. 1, reference numeral 24 identifies a breast shield element of a transparent material, which breast shield element 24 has a flange 26 and a nipple tunnel 28. Next to a free inner end 30 of the nipple tunnel 28, FIG. 1 shows a two-way valve element 32 which two-way valve element 32 can be mounted on the free inner end 30 of the nipple tunnel 28.

The breast shield element 24 is provided with threads 34 arranged circumferentially spaced relative to each other on the outer circumference of the nipple tunnel 28.

Reference numeral 36 identifies a milk container consisting of a spherical container shell element 38 and a lid element 40. This lid element 40 comprises a flat lid section 42 and a longish nipple tunnel receptacle 44. Reference numeral 46 identifies a milk chamber defined between the inner wall of the spherical container shell element 38 and the flat lid section 42. Into said milk chamber 46, the nipple tunnel receptacle 44 extends.

A top section of the spherical container shell element 38 is provided with a spout 48. The flat lid section 42 slidingly holds a spout closure element 50, which is adapted to assume three different positions.

In FIG. 1, the lid element 40 is connected with the spherical container shell element 38 by means of a hinge 52. Both, the lid element 40 and the spherical container shell element 38 provide surfaces defining the hinge 52. Cooperating surfaces of the hinge 52 allow pivoting of the lid element 40 toward the container shell element 38.

As derivable from FIG. 2, the lid element is provided with a container seal 54 provided on the circumference of the flat lid section 42 and cooperating with the inner surface of the container shell element 38 to sealingly enclose the milk chamber 46. In this closed position, the spout closure element 50 is arranged in a securing position in which the spout closure element 50 cooperates with the container shell element 38 to secure the lid element 40 in place. For releasing the lid element 40, the spout closure element 50 can be slid radially inward away from the outer circumference of the spherical container shell element 38 to disengage from this container shell element 38. In this removal position, the lid element 40 may be pivoted about the hinge 52 and finally detached from the container shell element 38. In a position intermediate of said removal position and the securing position of the lid element 40, the spout closure element 50 will still cooperate with the container shell element 38 to hold the lid element 40 in place while uncovering the spout 48. Thus, with the lid element 40 held in place, milk received within the milk chamber 46 can be poured out through the spout 48. This intermediate position is the pouring position of the spout closure element 50.

The inner circumference of the nipple tunnel receptacle 44 is provided with threads 56 cooperating with the threads 34 of the nipple tunnel 28 to secure the breast shield element 24 against the milk container 36 when the nipple tunnel 28 projects through the bore 10 of the housing 2 and is received within the nipple tunnel receptacle 44.

Figure 3:
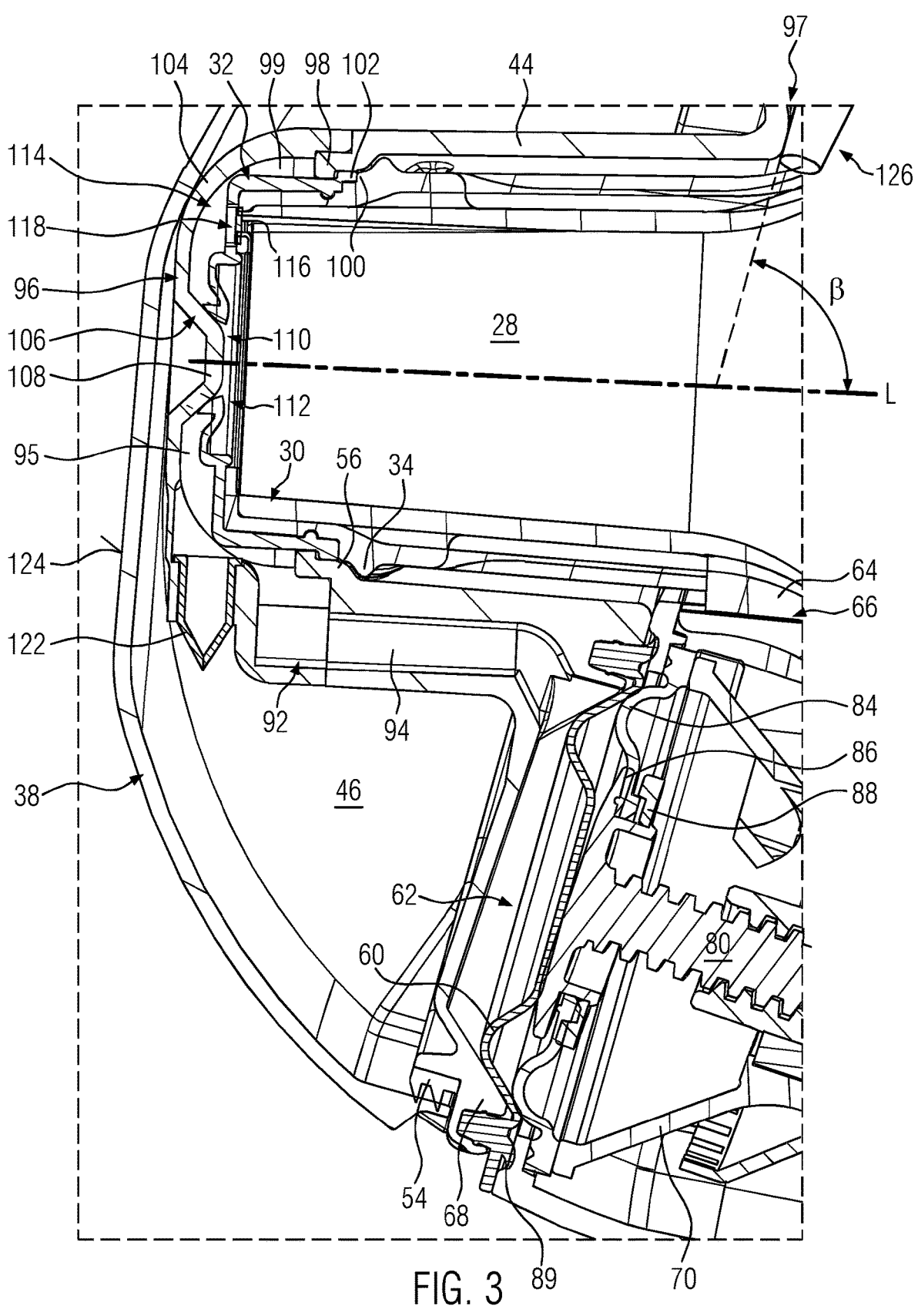
FIG. 3 is an enlarged detail of FIG. 2.

Reference numeral 60 identifies a membrane, which is sandwiched as an individual element between the milk container 36 and the housing 2 closing a membrane working chamber 62 formed by a trough projecting from the flat lid section 42 toward the milk chamber 46, see FIG. 3

FIGS. 1 and 4 elucidate alignment ribs 64 provided at a transition between the flange 26 and the nipple tunnel 28. Three alignment ribs 64 are provided, which alignment ribs 64 serve different purposes. FIG. 4 shows proper orientation of the breast shield element 24 relative to the housing 2. The lower alignment rib 64 is to be arranged at the lowest point of the nipple tunnel when the breast pump is in an upright position in which upright position the top section 8 defines the highest point of the breast pump. In such orientation, the longitudinal axis L defining the longitudinal axis of the nipple tunnel 28 and the nipple tunnel receptacle 44 extends essentially horizontal.

In addition, the milk container 36, in particular the lid section 42 thereof and/or the nipple tunnel receptacle 44 and/or the nipple tunnel 28 may be provided with optical marks or guidelines which are assigned to each other and will allow optical proof of proper alignment of the breast shield element 24 and the milk container 36. The optical marks or guidelines may confirm proper alignment if the optical marks or guidelines coincide or are aligned e.g. parallel with each other.

As derivable from FIG. 3, the housing 2 defines alignment rib receptacles 66, which each receive the assigned alignment rib 64 of the breast shield element 24 when properly connecting the breast shield element 24 with the housing by means of screwing the threads 34, 56 against each other. As the outer contour of the milk container 36 corresponds to the outer contour of the housing 2 at the front surface 20, proper positioning of the milk container 36 relative to the housing 2 can easily be controlled. As the front surface 20 as well as the lid section 42 are flat, both, the milk container 36 and the housing 2 are designed to abut against each other while sandwiching the membrane 60 in between, which membrane 60 is snapped within an outer rim 68 of the trough forming the membrane working chamber 62; compare FIGS. 2 and 3.

Proper positioning of the breast shield element 24 relative to the housing 2 will be heard by a click of the alignment ribs 64 snapping into the receptacles 66. Cooperation of the alignment ribs 64 with the alignment rib receptacles 66 also avoids unintentional rotational movement between the breast shield element 24 and the housing 2 around the longitudinal axis L. The housing 2 and the milk container 36 will have assigned positive closure members to avoid rotational movement between those two elements 2, 24. For example, one of the housing 2 and the milk container 36 may have a rib and the other may have a slot adapted to receive the rib to prevent rotational movement.

Figure 7:
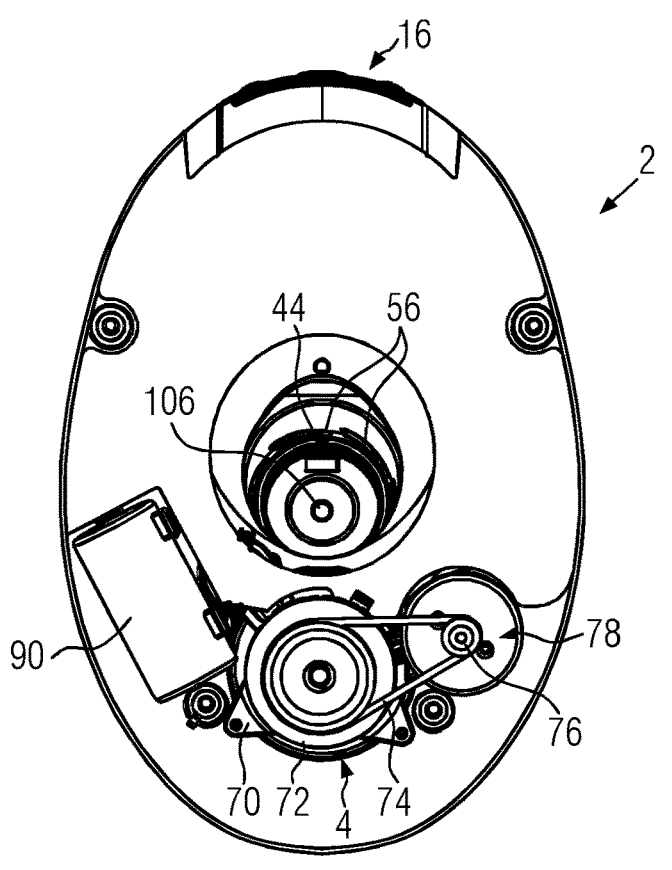
FIG. 7 is a cross-sectional view along line VII-VII according to FIG. 2.

FIG. 3 shows details of the aggregate 4 which in combination with FIG. 7 can be understood as comprising a drive housing 70 rotatably supporting a nut element 72 which nut element 72 cooperates with a drive belt 74 to drivingly connect the nut element 72 with a drive shaft 76 of an electric drive motor 78.

The nut element 72 cooperates with a piston 79 comprising a spindle 80. The nut element 72 is rotatably supported by a bearing 82 held by the drive housing 70. Between the drive housing 70 and walls of the housing 1, a housing bellows 84 is sandwiched and thus sealed against the housing 2, which housing bellows 84 is sandwiched between a cap section 86 of the spindle 80 and a disc element 88. The housing bellows 84 seals a working space inside the housing 2 and this the front side of the piston 79 formed by the cap section 86. Inside said working space the piston 79 formed by the spindle 80 and the cap section 86 will be moving linearly in a reciprocating fashion. The disc element 88 can be secured against the cap section 86, e.g. by means of gluing, welding or hot pressing of projections which penetrate the housing bellows and the disc element 88 and the like.

FIG. 3 shows, that in the assembled state the membrane 60 is sealingly pressed against an annular rim of the housing 2, which annular rim surrounds the housing bellows 84. The housing bellows 84 is arranged essentially flush with the front surface 20 of the housing 2. Respective annular rim has a surface geometry formed by an annular groove adapted to cooperate with a sealing lip 89 of the membrane 60 to effect a tight seal. As mentioned before, the housing bellows 84 is likewise sealed against an inner side of the housing 2, i.e. the annular rim thereof. This in turn leads to the formation of a clamp space 91 between the membrane 60 and the housing bellows 84. Thus, the reciprocating movement of the piston 79 will vent the clamp space 91 at the commencement of the pumping session. The seal will prevent ambient air from entering into the clamp space 91 as the piston pulls the membrane 60 towards the housing 2. As a consequence the membrane 60 contacts and is coupled to the piston 79 by a vacuum clamp. Thus, during the pumping session the piston 79 not only advances the membrane 60 towards the membrane working chamber 62 but also pulls the membrane 60 towards the housing 2 to expand the membrane working chamber 62. This is one example for the piston 79 moving the membrane 60.

Reference numeral 90 identifies a rechargeable battery/accumulator adapted to energize the electric drive motor 78 and being electrically coupled with a USB interface below the cover 18 for recharging the battery 90, see FIG. 7.

In particular, FIG. 3 elucidates details of a pumping chamber 92 including the membrane working chamber 62, a pumping channel 94, an outlet space 95 provided between the free inner end 30 of the nipple tunnel 28 and a forward closed end 96 of the nipple tunnel receptacle 44 and an annular milk path 99. As derivable from FIG. 3, the front surface 20 of the housing 2 is inclined relative to the longitudinal axis L by an angle ß of about 80°. A gap 97 is provided between the milk container 36 and the housing 2 extending with this angle of inclination ß relative to longitudinal axis L of the nipple tunnel. In FIG. 2, the gap 97 has a very small thickness. The gap 97 may be larger to receive textile material of a bra (not shown).

Distal of the threads 34, 56, the nipple tunnel receptacle 44 provides a sealing projection 98 projecting radially over a sealing projection 100 of the nipple tunnel 28. Those sealing projections 98, 100 sandwich in between the proximal end of the two-way valve element 32 thereby providing an outer seal 102. This outer seal 102 seals the outlet space 95 and thus the pumping chamber 92 against an annular ring space provided between the nipple tunnel 28 and the nipple tunnel receptacle 44.

As in particular derivable from FIG. 3, the forward closed end 96 of the nipple tunnel receptacle 44 is provided by a nipple tunnel receptacle closure cap element 104, which is secured to the nipple tunnel receptacle 44 e.g. by welding.

The closed end 96 has a projection 106 defining a flat closing surface 108 cooperating with the two-way valve element 32. The center of the two-way valve element 32 has a reflux opening 110, which in cooperation with the flat closing surface 108 defines a reflux valve 112.

In FIG. 3, reference numeral 114 identifies a milk outlet opening cooperating with a wall section 116 projecting radially inwardly from the nipple tunnel 28 and provided by the breast shield element 24. This wall section 116 in combination with the milk outlet opening 114 defines a milk outlet valve 118 separating the nipple tunnel 28 from the outlet space 95.

As derivable from FIG. 3, the lower end of the outlet space 95 is provided with a container valve 122 sealing the pumping chamber 92 against the milk chamber 46. This container valve 122 prevents reflux of milk contained within the milk chamber 46 into the outlet space 95. The container valve 122 is formed by a separate element formed made of a soft elastomeric material and attached to the milk container 36, specifically, the nipple tunnel receptacle 44. Preferably, the container valve 122 is assembled when connecting the closure element 104 to the nipple tunnel receptacle 44. Thus, the container valve 122 may be affixed to the lid element 40 or may be separatable from the lid element 40 for cleaning or replacement. The two-way valve element 32 is also made from soft elastomeric material.

In FIG. 3, reference numeral 124 identifies a round support surface of the milk container 36. Essentially on an axis intersecting with the center of the support surface 124 and extending perpendicular to said support surface 124, the center of gravity of the breast pump is arranged. Thus, when being supported by means of the support surface 124 on a horizontal plane, the breast pump will assume an upright position with the longitudinal axis L essentially extending vertically. In such position, the spout 48 assumes the highest point of the milk chamber 46. In other words, the lid section 42 is slightly inclined relative to the horizontal plane.

Various means are or can be provided to determine milk flow and milk flow conditions and/or proper nipple alignment. In FIG. 3, reference numeral 126 identifies a sensor in the form of an optical camera which is directed through a lens (not shown) towards the transparent nipple tunnel 28. Thus, respective sensor 126 may be used to transmit images onto a mobile device to imagine nipple arrangement within the nipple tunnel 28 or milk flow as the breast pump is in operation. Reference numeral 126 may as well indicate a sensor unit directing a light beam towards the milk inside the milk container 36 and receive the reflected light, which signal is processed for determining the amount of the expressed milk. If the calculated fill level reaches a threshold value the fill level indicator 14.1 will be activated to indicate filling of the milk container 36.

As clearly derivable from FIG. 5, the container shell element 38 is made of a frosted transparent material which is partially clear transparent to form a window 128. This window 128 is essentially aligned with the user interface 16. Accordingly, the width of the window 128 near the outer rim of the milk container 36 as depicted in FIG. 5 corresponds with the circumferential extension of the elements of the user interface 16. The window 128 will allow the user to view the transparent nipple tunnel 28 during use of the breast pump. Thus, an element 12 or an optical indicator 14 of the user interface 16 can be viewed from above along with the nipple tunnel when using the breast pump.

FIG. 5 exemplifies an angle α to identify the width of the window 128 at the top section 8 and the circumferential extension of the elements 12 of the optical indicator. α may be in the range of between 120° to 70°. In the drawings, reference numeral 129 identifies a circumferential rim on the circumferential surface of the housing 2 adjacent to the bore 10, which bore 10 is adapted to receive the breast shield element 24 and through which bore 10 the nipple tunnel 28 projects. On said circumferential rim 129, the elements of the user interface 12 are arranged within the window angle α such that the user will see all user interface elements 12 when wearing the breast pump in proper position, i.e. with the spout 48 being the highest point of the breast pump when using the pump sitting or standing.

As evident from FIG. 1, not only the breast shield element 24 is completely made of a clear transparent material, but also the lid element 40. To estimate the amount of expressed milk contained within the milk chamber 46, the spherical container shell element 38 as well as the lid element 40 are each provided with scale lines 130.

FIG. 5 furthermore shows that the maximal radial extension of the milk container 36 is smaller at least at the top section 8 than the radial extension of the housing 2. Thus, the user interface 16 radially projects the outer contour of the milk container 36.

Figure 8:
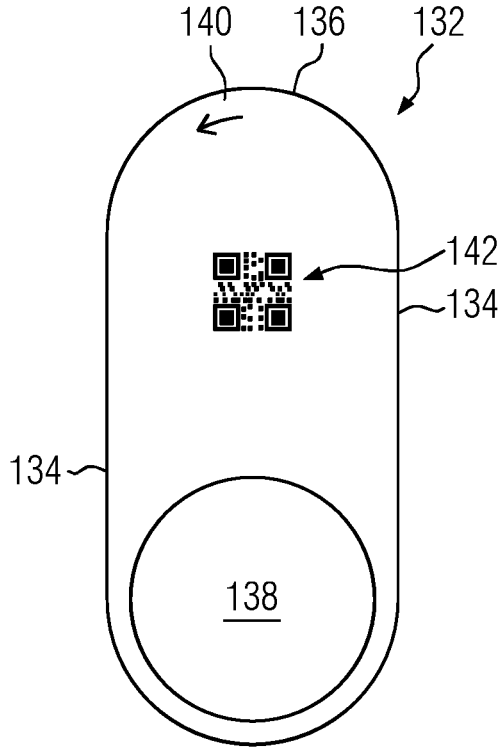
FIG. 8 is a perspective front view of the sheet element of the first embodiment

With reference numeral 132 a sheet element is identified in FIG. 5, which sheet element 132 per se is shown in FIG. 8. The sheet element 132 is made of a sheet material. In the present embodiment, the sheet material is a thin plastic sheet. The sheet element 132 has parallel longitudinal edges 134 which extend parallel to each other and are connected by semicircular end surfaces 136. The lower end surface 136 surrounds a round opening 138, which can be slid over the nipple tunnel 28. In such a position, the sheet element 132 will project with its free end 140 the milk container 36. An arrow is provided on said free end 140 which visualizes turning movement of the milk container 36 for releasing the threaded connection between the milk container 36 and the breast shield element 24. Reference numeral 142 identifies a QR code, which will bring the user to a menu transmitted via Internet. The pump may be assembled with or without the sheet element 132.

For assembly, the container shell element 38 is connected with the lid element 40. For this, the hinge 52 is formed and the lid element 40 is pivoted towards the shell element 38. The contained seal 54 will contact the inner surface of the shell element 38 and the snap connection will releasably secure this position. Then, the spout closure element 50 is shifted into the securing position, thereby securing the position of the lid element 40 relative to the container shell element 38. Before laying the housing 2 against the lid section 42, the membrane 60 is secured against the lid element 42. After the housing 2 has been laid with its front surface 20 against the flat lid section 42, the protective membrane 60 is sandwiched and thus secured between those two functional elements, i.e. the milk container 36 and the housing 2.

Next, the breast shield element 24 with the two-way valve element 32 secured against the free end 30 of the nipple tunnel 28 will be pushed through the bore 10. The breast shield element 24 may be rotated about 90° to 180° in order to engage the threads 34 and 56 for a threaded connection. After the alignment ribs 64 snap into the alignment rib receptacles 66, the user is aware of proper positioning of the breast shield element 24 relative to the housing 2 and the milk container 36.

Next, the assembled breast pump may be laid against the breast of the user. Proper alignment of the nipple before operating the breast pump can be confirmed e.g. through the window 128. After confirmation of proper nipple alignment, the user will initiate pumping operation by activating element 12.2.

Disassembly of the breast pump will be carried out in a reversed consequence as described above for assembling the breast pump. All parts except the housing 2 can be dish-washed or sterilized under steam.

During use, a full milk container 36 may be removed by unscrewing the milk container 36 relative to the breast shield element 24 thereby disengaging the threads 34, 56. A fresh empty milk container 36 may be attached to the breast shield element 24 if need arises without removing the breast shield element 24 from the breast of the user.

For operation, a breast identified with reference number 150 in FIGS. 9a to c and thus the nipple will be arranged within the nipple tunnel 28. Proper alignment can be observed through the window 128 from above. As the breast 150 contacts the breast shield element 24, a nipple chamber 152 is formed, which is sealed by the breast 150 towards the flange 26 of the breast shield element 24, which nipple chamber 152 is provided by the remaining volume of the nipple tunnel 28.

For complying best with the anatomic form of the breast 150, the breast shield element 24 has a specific geometry identified in FIG. 2. In this embodiment, the breast shield element 24 forms three sections, namely a tunnel section 154, which is essentially cylindrical and extends along the longitudinal axis L, a flat section 158, which defines the outer rim of the flange 26 and which extends essentially perpendicular to the longitudinal axis L, and an conical section 156, which is arranged between the tunnel section 154 and the flat section 158. This conical section 156 is inclined relative to the longitudinal axis by an angle γ of about 105°+/−12° preferably 105°+/−6°. In other words, the conical section 156 provides an abutment surface for the breast 150 which is conical with an inner inclination or opening angle of about 105°.

Next, the pump is activated. As a consequence, the spindle 80 and thus the cap section of this piston like element will move towards the membrane 60, thereby expelling remaining air from the space between the housing bellows 84 and the protective membrane 60. Upon further movement of the spindle 80 towards the membrane working chamber 62, residual air will be forced out of the membrane working chamber 62 through the container valve 122 into the milk chamber 46, which air is vented trough e.g. the spout 48. As the spindle 80 is reversed, the vacuum within the chamber between the housing bellows 84 and the protective membrane 60 will make the later follow the movement of the cap section 86 of the spindle 80. As a consequence, the volume of the membrane working chamber 62 is enlarged and thus a volume of the pumping chamber 92 is expanded, which results in a negative pressure being built up in the pumping chamber 92. The reflux valve 112 is closed. The negative pressure will build up in the nipple tunnel 28 through the open milk outlet valve 118—see FIG. 9a. Extracted milk is drawn through the milk outlet opening 114 in the expansion cycle of the aggregate 4. In an contraction cycle, in which the housing bellows 84 and thus the protective membrane 60 is moved towards the membrane working chamber 62 to reduce the pumping chamber volume 154, the milk outlet valve 118 will close. The suction pressure within the pumping chamber 92 will be reduced, i.e. the pressure will rise-see FIG. 9b. Until a reduced threshold suction pressure is reached within the nipple tunnel 28, the reflux valve 112 will remain open. Thus, a negative pressure of about 20 mm Hg will be maintained as a minimum baseline suction pressure within the nipple tunnel 28 as the pumping chamber 92 is fully contracted—see FIG. 9c. At appropriate pressure difference, milk will flow through the container valve 122, which is a one-way valve, into the milk chamber 46. In the expansion cycle, in which the housing bellows 84 and thus the protective membrane 60 is moved towards the drive housing 70, the suction force within the pumping chamber 92 is increased. Eventually, the container valve 122 as a one-way valve will close to prevent reflux of milk from the milk chamber 46 into the pumping chamber 92. The milk outlet valve 118 will open to allow milk to flow from the nipple tunnel 28 into the outlet space 95 of the pumping chamber, which pumping chamber 92 is essentially completely filled with milk.

Thus, the level of extracted milk within the milk chamber 46 builds up during operation of the pump while the nipple tunnel 28 is filled with milk and the nipple is constantly provided within a negative pressure environment.

In the following, further embodiments of the breast pump according to the invention will be discussed hereinafter. Where applicable, reference numbers as mentioned before will be assigned to the respective component. In each of the embodiments, a varying suction pressure within the nipple tunnel may be achieved as discussed before. Moreover, the piston within the housing discussed previously, which piston is coupled to a membrane is arranged in any of the embodiments. Nevertheless, it is worth noting that other means may be provided cyclically drive the membrane, e.g. by an internal pressure source within the housing. Yet, a mechanical activation of the membrane is preferred.

The second embodiment 200 has a housing 2 with two sections, namely a housing base 202 and a housing ring 204, which housing ring 204 defines the bore 10 for receiving the nipple tunnel 28. Accordingly, the housing 2 has a basket-shaped constitution, which is in particular visible from FIG. 10. The upper surface of the base 202 is planar and defines an abutment surface for the milk container 36, which milk container 36 has a triangular shape in side view (compare FIG. 11 or 12).

The nipple tunnel 28 is formed by a breast shield element 24 comprising the tunnel section 154, the conical section 156 and the flat section 158. The tunnel section 154 has a distal end which is open. Respective distal end is received within a breast shield sleeve 206. A cylindrical part of the breast shield sleeve 206 may be telescopically arranged with the distal end of the tunnel section 154. The breast shield sleeve 206 may be releasably coupled with the breast shield element 24 by sliding the tunnel section 154 into the breast shield sleeve 206. The parts may likewise be fixedly attached to each other e.g. by welding or gluing or may be formed as a unitary component, e.g. by ejection molding.

On the lower circumferential section, the breast shield sleeve 206 comprises a breast shield connector 208 fluidically coupling the distal end of the breast shield sleeve 206 with a membrane working chamber 62 provided by a membrane support section 210, which is adapted to form the membrane working chamber 62 as the membrane 60 is laid against the membrane support section 210. The membrane support section 210 forms part at least of the breast shield sleeve 206. The membrane working chamber 62 is in fluid communication with a channel arranged within and surrounded by the breast shield connector 208. This channel forms part of the pumping chamber 92.

In the second embodiment 200, the membrane 60 may be releasably secured to either the membrane support section 210 or the housing 2.

As in the previous embodiment, the milk container 36 has a container shell element 38 and a lid element 40. The milk container 36 defines a nipple tunnel receptacle, which circumferentially projects around the nipple tunnel 28 and/or the cylindrical portion of the breast shield sleeve 206. Thus, when inserting the breast shield element 24 along with the breast shield sleeve 206, which combination will hereinafter be referred to as the breast shield arrangement 212, the breast shield arrangement 212 securely couples the milk container 36 against the housing 2. As evident from the Figures, the nipple tunnel receptacle 44 is slightly inclined downwardly towards the closed end of the container shell element 38. Thus, the distal end of the nipple tunnel arrangement 212 can project into an open trough, which may likewise circumferentially project over the breast shield sleeve 206 to encompass the same in radial direction. In view of this, the oblique orientation of the breast shield arrangement 212 per se may secure all components of the second embodiment 200 in place by form-fit closures. In addition or alternatively, securing means like magnets or latches may be provided to hold the components together.

As is particularly evident from FIGS. 9 and 10, the spout 48 is arranged at the uppermost area of the milk container 30 as the breast pump is standing on the flat support surface 124. This flat support surface 124 may be provided by a soft elastomeric bottom element, which is shown in FIG. 12 and which due to its soft elastomeric properties assists the breast pump to attain a solid position. The bottom elements avoids sliding of the breast pump over the surface, which supports the breast pump. The bottom element 260 is releasably secured to the housing 2. Thus, the bottom element 216 can be cleaned, e.g. dish washed. The bottom element 216 has a flap 280 for dismounting the bottom element 216 from the housing 2.

As is particularly evident from FIG. 12, the upper surface of the housing base 202 extends horizontally and so does the corresponding lower surface of the milk container 36. This lower surface provides the base for supporting the milk container 36 on a flat surface with the spout 48 closed by the spout closure element 50 being the highest point. In the embodiment, the spout closure element 50 is round and made of silicone or the like. The lid element 40 provides a round receptacle for the spout closure element 50, which may hold the spout closure element 50 in place. The spout closure element 50 usually has a projection which is received within the spout 48 for proper closure of the spout 48 and securing the spout closure element 50.

As evident from FIGS. 10 and 14, the container shell element is made of transparent clear plastic material. However, only a central window section 220, which is surrounded by a frosted section 222. As evident, the window section 220 is positioned in the middle of the pump in width direction and the upper section of the container shell element 38 being directed to the user when wearing the breast pump. The width of the window section 220 corresponds with the width-wise extension of the user interface.

Details of the user interface are depicted in FIG. 14. In addition to the elements already discussed with respect to the first embodiment and being identified with respective reference numerals, the circumferential rim 129 is provided with an indicator 14.3 for indicating the Bluetooth status, i.e. whether the breast pump is connected with a mobile device via Bluetooth. The element 12.6 of the user interface will allow the user to switch from stimulation to expression mode and is referred to as the let-down button 12.6. All elements of the user interface 12 are covered by a soft elastomeric material which is flush with the hard elastic material forming the housing 2.

FIG. 15 elucidates the pumping chamber 92, which extends between the membrane working chamber 62, and the breast shield connector 208, i.e. the channel formed therein. The pumping chamber 92 also comprises an annular section surrounding the distal end of the breast shield arrangement 212. As before discussed for the first embodiment, valve elements can be provided near the distal end of the breast shield arrangement 212.

In the second embodiment 200, the housing 2 comprises at least one light source, which illuminates the items of all elements 12 of the user interface and all optical indicators 14. Moreover, light is guided through the transparent portions of the milk container 36 or the breast shield element 24 to in particular guide the light into the nipple tunnel 28. The light is decoupled within the nipple tunnel 28, e.g. by frosted areas or lenses. Thus, the user of the breast pump will be able to control proper nipple alignment within the nipple tunnel 28 at night. The basket-shaped form of the housing 2 will to a great extent shed the light within the milk container 36 and the breast shield arrangement 212 to avoid scattering of light to ambient. Accordingly, illumination of the breast pump is focused to the nipple tunnel 28 and the illumination of the elements 12 of the user interface 16 and the optical indicators 14.

In contrast to the first embodiment, the elements for switching between left and right use, which elements are identified with reference numerals 12.4 and 12.5 are provided on the outer circumferential surface of the housing base 202, i.e. specifically in the middle of this housing base 202 (compare FIG. 10). At night, the user will feel the respective elements 12.4/12.5 of the user interface. Below those elements and visible e.g. in FIG. 10 below respective elements, the housing base 202 has an ON/OFF button 12.7 as a further element of the user interface.

FIGS. 16 through 20 exemplify a third embodiment 300, having a milk container 36 arranged below a housing 2, which housing 2 receives the distal end of the breast shield arrangement 212, which breast shield arrangement 212 comprises a breast shield sleeve 206, which is connected to a membrane support section 210 to be coupled with the membrane 60. The membrane support section 210 extends radially from the circumferential surface of the breast shield sleeve 206. The housing 2 comprises a nipple tunnel receptacle 44 and a longitudinal slot 302 adapted to receive the membrane support section 210 and the membrane 60 attached thereto. Within the slot 302, the membrane 60 may be mechanically coupled to the piston (not shown).

As evident from FIG. 19, expressed milk is drawn in an annular space surrounding the distal end of the breast shield sleeve 206. By gravity and/or pressure difference generated by the piston 79 moving the membrane 60 in a reciprocating fashion to express milk from a breast received within the nipple tunnel 28. FIG. 20 exemplifies the position of the membrane 60 within the slot 302. As mentioned above, the pumping chamber may have valves as described in connection with the first embodiment. While the milk container 36 when using the breast pump is arranged below the housing 2 and thus expressed milk is likely to flow downward into the milk container 36, the milk can as well be transferred into the milk container 36 without the performance of the valves and the pressure differences within the milk container as described before. Thus, the milk can simply drip from the nipple tunnel 28 into the milk container 36.

As evident in particular from FIGS. 16 and 18, the window section 220 is a separate component made of transparent material partially frosted, which is joined to opaque material predominantly forming the housing 2. Joining can be obtained e.g. by composite ejection molding, welding or gluing. The transparent component part forming the window section 220 has lateral walls 304 which project into the housing 2 to allow direct view by the user through the window section 220 onto the nipple tunnel 28. The transparent material may be arranged flush with the opaque material on the outer circumferential surface of the housing 2. Alternatively, a trough with at least a transparent bottom may be formed on the outer circumference of the housing 2 which trough projects into the housing, thus, forming a recess on the outer surface of the housing.

At least one light source within the housing 2 is adapted to illuminate the window section 220. The lateral walls 304 may serve as light guides and light panels which illuminate the space between them providing a free view to the nipple inside the nipple tunnel 28.

FIG. 21 onwards elucidate a fourth embodiment 400, in which the milk container 36 is sandwiched between the flange 26 of the breast shield element 24 and the housing 2. As in the previous embodiment, the middle component, here the milk container 36, will be mechanically coupled to the other components just by being projected at least in part by the nipple tunnel 28. The nipple tunnel arrangement 212 mechanically locks within the housing 2. Means for proper positioning the milk container 36 relative to the housing 2 and/or the breast shield element 24 may be provided as e.g. described for the first embodiment. While a front surface 22 of the housing 2 is slightly inclined in distal direction when using the pump, the user of the pump will still be able to view the user interface 16 and the optical indicators to obtain information of operational status of the pump and control the same.

As in the previous embodiments, the spout 48 assumes the highest position of the pump when resting the breast pump on the support surface 124; compare FIG. 21. The milk container 36 is made of a transparent material allowing to view proper nipple alignment within the nipple tunnel 28 through the milk container 36 and through the nipple tunnel 28. The breast shield element 24 is made of clear transparent material.

LIST OF REFERENCE SIGNS 2 housing
4 aggregate
6 bottom section
8 top section
10 bore
12 elements of a user interface
12.1 suction pressure up
12.2 play/pause
12.3 suction pressure down
12.4 left breast pumping
12.5 right breast pumping
12.6 let down
12.7 on/off
12.8 USB slot
14 optical indicator
14.1 fill indicator
14.2 battery level indicator
14.3 blue tooth status
16 user interface
18 cover
20 front surface
22 rear surface
24 breast shield element
26 flange of the breast shield element
28
30 nipple tunnel
30 free inner end
32 two-way valve element
34 thread
36 milk container 38 container shell element 38
40 lid element
42 lid section
44 nipple tunnel receptacle
46 milk chamber
48 spout
50 spout closure element
52 hinge
54 container seal
56 thread
60 membrane
62 membrane working chamber
64 alignment rib
66 alignment rib receptacle
68 outer rim
70 drive housing
72 nut element
74 drive belt
76 drive shaft
78 drive motor
79 piston
80 spindle
82 bearing
84 housing bellows
86 cap section
87 drive means
88 disc element
89 sealing lip
90 battery
91 clamp space
92 pumping chamber
94 pumping channel
95 outlet space
96 closed end
97 gap
98 sealing projection
99 annular milk path
100 sealing projection
102 outer seal
104 nipple tunnel receptacle closure cap element
106 projection
108 flat closing surface
110 reflux opening
112 reflux valve
114 milk outlet opening
116 wall section
118 milk outlet valve
122 container valve
124 support surface
126 sensor
128 window
129 circumferential rim
130 scale line
132 sheet element
134 longitudinal edge
136 end surface
138 opening
140 free end
142 QR code
150 breast
152 nipple chamber
154 tunnel section
156 conical section
158 flat section
150 breast
152 nipple chamber
154 tunnel section 156 conical section
158 flat section
200 second embodiment
202 housing base
204 ring section
206 breast shield sleeve
208 breast shield connector
210 membrane support section
212 breast shield arrangement
214 trough
216 bottom element
218 flap
220 window section
222 frosted section
300 third embodiment
302 slot
304 lateral wall
400 fourth embodiment
L longitudinal axis
α window angle
β angle between front surface 20 of the housing 2 and longitudinal axis L
γ inner inclination angle

The invention claimed is:

1. A breast pump shaped at least in part to fit inside a bra and comprising a housing including an aggregate drivingly coupled with a membrane, a breast shield element including a nipple tunnel adapted to receive a nipple, and a milk container adapted to contain a predetermined amount of expressed milk, wherein the breast shield element and the milk container are detachable from the housing and wherein the membrane is detachable sealed against the housing, wherein the aggregate comprises a piston adapted to reciprocate within the housing, which piston moves the membrane, the pump comprising a pumping chamber defined in part by the membrane, which pumping chamber is in fluid communication with the nipple tunnel, the membrane being releasably received between the milk container and the housing such that the membrane is arranged opposite to the piston, and the membrane and a drive end side of the piston are arranged in a clamp space, which is sealed to prevent ambient air from entering into the clamp space as the piston pulls the membrane towards the housing to expand a pumping chamber.

2. The breast pump according to claim 1, the housing at least in part circumferentially surrounds surrounding the nipple tunnel in radial direction of the nipple tunnel, wherein the breast shield element is rotatable held within the housing and/or the milk container and/or wherein the milk container is rotatable held within the housing and/or the nipple tunnel and wherein at least two of the breast shield element, the housing and the milk container comprise mating surfaces of a bayonet or of a screw connection.

3. The breast pump according to claim 1, the milk container comprising a spherical container shell element and lid element comprising a flat lid section and a longish nipple tunnel receptacle adapted to receive at least a part of the nipple tunnel and wherein the shell element and lid element are detachable secured against each other.

4. The breast pump according to claim 3, further comprising a spout closure element moveably held by the lid element and adapted to secure the lid element against the container shell element in a securing position, to allow removal of the lid element from the container shell element in a removal position and to allow pouring of the expressed milk out of the milk container while securing the lid element against the container shell element in a pouring position, which pouring position is intermediate of the securing position and the removal position.

5. The breast pump according to claim 1, further comprising a two-way valve element interdisposed between a free inner end of the nipple tunnel and the milk container, wherein the valve element comprises a milk outlet valve cooperating with the nipple tunnel to allow expressed milk to be drawn from the nipple tunnel under a predetermined suction pressure and a reflux valve cooperating to reflux of milk into the nipple tunnel until the pressure in the nipple tunnel has reached a reduced threshold suction pressure.

6. The breast pump according to claim 1, further comprising a pumping chamber defined between the nipple tunnel and a milk chamber defined by the milk container, wherein a milk outlet valve and a reflux valve are provided between the pumping chamber and the nipple tunnel, wherein a container valve is provided between pumping chamber and the milk chamber, wherein the milk outlet valve is adapted to allow milk to flow from the nipple tunnel into the pumping chamber, wherein the reflux valve is adapted to allow milk to flow from the pumping chamber into the nipple tunnel and wherein the container valve is adapted to allow milk to flow from the pumping chamber into the milk chamber (46) and wherein the milk outlet valve, the reflux valve and the container valve are each activated by pressure difference between the pumping chamber and the nipple tunnel and the pumping chamber and the milk chamber, respectively.

7. The breast pump according to claim 5, the two-way valve element providing an outer seal sealing the pumping chamber against the outer circumference of the nipple tunnel and/or the nipple tunnel receptacle.

8. The breast pump according to claim 1, the milk container comprising a spherical container shell element having a front section arranged in longitudinal extension of the longitudinal axis of the nipple tunnel, wherein the spherical container shell element has a flat support surface.

9. The breast pump according to claim 1, the milk container comprising a transparent window which in radial direction of the nipple tunnel is aligned with elements of a user interface.

10. The breast pump according to claim 9, the milk container comprising a nipple tunnel receptacle adapted to receive the nipple tunnel, wherein the nipple tunnel receptacle and the nipple tunnel are each at least partially made of a transparent material, and wherein the nipple tunnel receptacle is provided with at least one guide line allowing visual nipple alignment within the nipple tunnel.

11. The breast pump according to claim 1, wherein the nipple tunnel and the milk container are at least partially made of a transparent material to allow the user to view the nipple tunnel in a use position through the milk container and further comprising a light source adapted to direct a light beam on the nipple tunnel.

12. The breast pump according to claim 1, the aggregate comprising a reciprocating drive means which is coupled to a protective membrane element, which seals a membrane working chamber arranged below the nipple tunnel when the breast pump is in a use position in which a longitudinal extension (L) of the nipple tunnel extends essentially in a horizontal direction.

13. The breast pump according to claim 1, further comprising, an internal pump for providing a directed flow of milk within the breast pump comprises at least two valves for directing the milk flow and a protective membrane element for driving the milk by direct contact with the milk, which at least two valves and said protective membrane element are received in the milk container.

14. The breast pump according to claim 12, the protective membrane element being coupled to said drive means by a vacuum seal.

15. The breast pump according to claim 1, and at least two-valves for directing the milk flow and/or a protective membrane element for driving the milk are arranged outside of the housing.

16. The breast pump shaped according to claim 1, the breast shield element having a flange which is at least in part defines an conical section with an inner opening angle γ of 105°+/−10°.

17. A method for operating a breast pump shaped at least in part to fit inside a bra and comprising a housing including an aggregate, a breast shield element including a nipple tunnel adapted to receive a nipple, and a milk container defining a milk chamber adapted to contain a predetermined amount of expressed milk, wherein a pumping chamber is defined within the breast pump, a pumping chamber volume thereof being variable by a moveable membrane, wherein a milk outlet valve is provided between nipple tunnel and the pumping chamber and wherein a container valve is provided between the pumping chamber and the milk chamber, in which method when the breast shield element is laid against a breast a nipple chamber is defined in the nipple tunnel between a free end of the nipple tunnel and the breast, in which method expressed milk flows from the nipple chamber through the milk outlet valve into the pumping chamber and from the pumping chamber through the container valve into the milk chamber, wherein at commencement of pumping air is sucked out of the nipple chamber and the pumping chamber and transferred into the milk chamber, which air is released out of the milk chamber to ambient and that expressed milk replaces the air in the nipple chamber and in the pumping chamber and which milk builds a hydraulic coupling between the breast and the membrane such that movement of the membrane will be hydraulically transmitted to the breast inside the nipple tunnel.

\* \* \* \* \*